US005106956A

United States Patent [19]

Casellas et al.

[11] Patent Number: 5,106,956

[45] **Date of Patent: * Apr. 21, 1992**

[54] RIBOSOME-INACTIVATING GLYCOPROTEINS, MODIFIED BY OXIDATION OF THEIR OSIDIC UNITS AND REDUCTION, AND IN VIVO PROLONGED-ACTION IMMUNOTOXINS CONTAINING SUCH A GLYCOPROTEIN

[75] Inventors: Pierre Casellas; Bernard Bourrie, both of Montpellier; Xavier Canat, Saint-Georges D'Orques, all of France

[73] Assignee: Sanofi, Paris, France

[ * ] Notice: The portion of the term of this patent subsequent to Mar. 27, 2007 has been disclaimed.

[21] Appl. No.: 404,611

[22] Filed: Sep. 8, 1989

Related U.S. Application Data

[62] Division of Ser. No. 941,989, Dec. 15, 1986, Pat. No. 4,911,912.

[30] Foreign Application Priority Data

Dec. 20, 1985 [FR] France ............................... 85 18982
Aug. 12, 1986 [FR] France ............................... 86 11644

[51] Int. Cl.[5] ........................ C07K 17/02; C07K 15/28; A61K 39/44

[52] U.S. Cl. ................................ 530/391.9; 530/395; 530/397; 530/866; 530/863; 424/85.91

[58] Field of Search ............... 530/395, 397, 390, 391, 530/388; 424/85.91

[56] References Cited

U.S. PATENT DOCUMENTS

| | | | |
|---|---|---|---|
| 4,340,535 | 7/1982 | Voisin et al. | 530/388 |
| 4,368,149 | 1/1983 | Masuho et al. | 530/388 |
| 4,911,911 | 3/1990 | Casellas et al. | 424/85.91 |
| 4,911,912 | 3/1990 | Casellas et al. | 424/85.91 |

FOREIGN PATENT DOCUMENTS 88695 9/1983 European Pat. Off. .

OTHER PUBLICATIONS

Blair et al., (1983), J. Immunol. Methods 59:129–143.
Skilleter et al. (1985), Biochim. Biophys. Acta 842:12–21.
Vitetta et al., (1985) Cancer Drug Delivery 2:191–198.
Wawrzynczak et al. (1987) in Immunoconjugates Antibody Conjugates in Radioimaging and Therapy of Cancer (C-W Vogel, ed), N.Y., Oxford Univ. Press. pp. 28–55.
Olsnes et al., (1982), Pharmac. Ther. 15:355–381.

*Primary Examiner*—Christine Nucker
*Assistant Examiner*—Kay K. Kim
*Attorney, Agent, or Firm*—Bacon & Thomas

[57] ABSTRACT

Glycoprotein which inactivates ribosomes (GPIR) having the ribosome-inhibiting activity of the native GPIR and having a prolonged-action in vivo which is obtained by oxidation of its osidic units by the action of periodate ions, and simultaneous reduction with cyanoborohydride ions. Said modified glycoprotein may be coupled to an antibody or a fragment thereof in order to form an immunotoxin having a prolonged-action in vivo.

10 Claims, 3 Drawing Sheets

RIBOSOME-INACTIVATING GLYCOPROTEINS, MODIFIED BY OXIDATION OF THEIR OSIDIC UNITS AND REDUCTION, AND IN VIVO PROLONGED-ACTION IMMUNOTOXINS CONTAINING SUCH A GLYCOPROTEIN

This application is a division of application Ser. No. 941,989, filed Dec. 15, 1986, now U.S. Pat. No. 4,911,912.

The present invention relates to new medicinal molecules containing at least one antibody covalently bonded to a constituent of polypeptide type which inhibits protein synthesis and is derived from a glycoprotein (or a glycopeptide) whose polysaccharide units have been modified.

U.S. Pat. No. 4,340,535 and French Patent Applications no. 2 504 010 and no.2 516 794 describe the preparation of anticancer products, called conjugates, which are obtained by the coupling, by means of a covalent bond, of the A chain of ricin with antibodies or antibody fragments directed against antigens carried by the cell to be destroyed. The products of this type have been designated, and are designated in the present Application, by the generic name of immunotoxins.

Conjugates analogous to the previously described immunotoxins containing the A chain of ricin are known which are also suitable as anticancer drugs and result from the coupling, by means of a covalent bond, of antibodies or antibody fragments with other glycoproteins which inactivate ribosomes, such as, in particular, the gelonine extracted from Gelonium multiflorum (Eur. J. Biochem. 1981, 116, 447-454; Cancer Res. 1984, 44, 129-133) or the inhibitor extracted from Momordica charantia (MOM) (U.S. Pat. No. 4,368,149).

These glycoproteins which inactivate ribosomes (abbreviated to GPIR), and which have properties similar to those of the A chain of ricin, are substances with a molecular weight of the order of magnitude of 20,000 and 30,000 (Cancer Survey, 1982, 1, 489-520).

The term "glycoprotein which inactivates ribosomes", as used in the present description and also in the claims, denotes any substance which carries saccharide units belonging to the class of macromolecules which inactivate ribosomes and consequently inhibit protein synthesis in eucaryotic cells, as well as any fragment of the said substance which possesses the same inactivating property, it being possible for the said glycoprotein which inactivates ribosomes to be of natural or biosynthetic origin, being derived from a cell whose genotype has been modified for this purpose.

It is also known that the cytotoxic activity of these immunotoxins can be potentiated by a variety of adjuvant substances such as ammonium salts, various amines or certain carboxylic ionophores such as monensin or nigericin.

However, the therapeutic effects of immunotoxins, whether activated or not, can only manifest themselves fully on condition that the immunotoxin is capable, through its antibody part, of becoming localized in vivo, in the active form, on the target cells to be destroyed (sine qua non condition for any expression of immunotoxin activity). The capacity of the immunotoxin to become localized on the target depends first and foremost on the ability of the immunotoxin to remain in the bloodstream and the extracellular fluids, in the active form, for sufficient lengths of time for it to reach its target cells and at sufficient concentrations to give a high degree of occupation of the corresponding antigen sites.

Numerous studies have made it possible to establish the plasma elimination kinetics of immunotoxins after intravenous injection into various animal models. It has been found that, after injection, the plasma level of biologically active immunotoxin decreases very rapidly and very substantially. Thus, in a typical case involving rabbits, in a model using an immunotoxin built up by coupling the A chain of ricin, by means of a link containing a disulfide bridge, with a monoclonal antibody directed against the antigen T65 of human T lymphocytes (antibody T101), it is found that 97% of the immunotoxin present in the bloodstream at time 0 after injection disappears in 30 minutes and 99.9% disappears in 17 hours. This rapid disappearance of the immunotoxin quite obviously detracts from the expression of its complete cytotoxic capacity, the immunotoxin being prevented from durably saturating a high proportion of the target antigens carried by the cells to be destroyed. Moreover, a comparison of the plasma elimination kinetics of immunotoxins with those of the corresponding unconjugated antibodies shows by contrast that—as is well known—the antibodies remain in the plasma at a high level for relatively long periods of time. Now, even in the most highly purified immunotoxin preparations, there is always a certain residual level of unconjugated antibodies. Due to the effect of the differential rates of elimination of immunotoxins and antibodies, the unconjugated antibodies, which are initially very much in the minority, progressively become the majority component after a few hours, so these antibodies gradually compete to become powerful antagonists for the fixation of the immunotoxins to their targets.

Therefore, this clearly shows the value of enhancing the persistence of immunotoxins in the plasma, in their active form, so as to increase both the duration and degree of occupation of the target antigens and consequently to improve the therapeutic effects of the immunotoxins.

Furthermore, experiments involving in vivo localization of the immunotoxin containing the A chain of ricin, radiolabeled and then injected into animals with no specific target, have shown that the conjugate becomes localized preferentially in the liver during first few minutes after injection. The same applies to the A chain of ricin, which follows the same pattern when injected in the uncoupled form. This strongly suggests that the immunotoxin becomes fixed in the liver via the cytotoxic sub-unit contained in the immunotoxin.

It is known that the A chain of ricin is a glycoprotein whose polyosidic groups comprise especially mannose residues and N-acetylglucosamine residues, some mannose residues being in terminal positions (Agri. Biol. Chem., 1978, 42, 501). Also, receptors capable of recognizing glycoproteins containing these terminal mannose residues have been found to exist in the liver. It has also been shown that the glycoproteins recognized by these receptors—the latter being present essentially on the Kupffer cells—are rapidly eliminated from the bloodstream by fixation to these cells, which metabolize them. This is well documented especially in the case of beta-glucuronidase and in the case of ribonuclease B (Arch. Biochem. Biophys., 1978, 188, 418; Advances in Enzymology, published by A. Meister, New York, 1974; Pediat. Res., 1977, 11, 816).

Taken as a whole, this information shows that the rapid elimination of immunotoxins containing the A chain of ricin can be explained by the recognition of the mannose residues of the A chain of ricin by the hepatic cells and in particular the Kupffer cells.

The studies of plasma elimination kinetics carried out on other GPIRs, for example gelonine or MOM, after intravenous injection into the animal, have shown that, as in the case of the A chain of ricin, the plasma level of GPIR decreases very rapidly and very substantially after injection. Thus, in a typical case involving rabbits, after the injection of gelonine purified by the method described (J. Biol. Chem., 1980, 255, 6947–6953), it is found that 93% of the gelonine present in the bloodstream at time 0 after injection disappears in 1 hour and 99.99% disappears in 24 hours.

It is known that the oxidation of osidic structures, including those contained in glycoproteins, with periodate ions causes the scission of the carbon chain wherever two adjacent carbon atoms carry primary or secondary hydroxyls. If the two adjacent hydroxyls are secondary, as is generally the case in the cyclic oses present in GPIRs, oxidation produces two aldehyde groups on the carbons between which the scission has taken place.

It is also known that aldehyde functions are very reactive towards primary amine groups with formation of imines also known as Schiff's bases. Thus, the aldehyde groups formed during the oxidation reaction can react with primary amines carried by the peptide chain of glycoprotein and form undesirable intra- and/or intermolecular covalent bonds, leading to an instability of the oxidation product and often in the formation of insoluble polymers.

It is also known that the formation of Schiff's bases can be prevented if the aldehyde groups created by the periodate oxidation are quickly reduced into stable primary alcohol. Such reduction can be carried out with reducing agents such as borohydride ions. The cyanoborohydride ion is a particularly suitable reagent since the periodate ion and the cyanoborohydride ion can co-exist without the reducing agent making the periodate ion lose its oxidizing power, and vice versa.

It has now been found, absolutely unexpectedly, that, if the carbohydrate units of a GPIR are modified by the original process described hereinafter, a new molecule of GPIR is obtained which has the dual property of retaining its biological activities and of being eliminated very slowly from the blood stream after injection in superior animals or in humans. Said new modified GPIR which has retained the property of inactivating ribosomes and which has acquired because of the modification, a prolonged action in vivo, is denoted in the present application by the symbol GPIR-1a.

This original process consists in modifying the osidic units of the GPIR by simultaneous reaction with periodate ions and cyanoborohydride ions. Thus, the aldehyde groups created by the oxidation with periodate are reduced as and when they appear, into stable primary alcohol groups, by the cyanoborohydride ions, thus preventing the undesirable reactions with the amino groups of the GPIR and permitting the obtention of a stable and very soluble product.

It has also been found that, if this new molecule of prolonged-action GPIR is coupled with antibody or antibody fragments, the resulting conjugates retain the known biological properties of immunotoxins and exhibit slow plasma elimination kinetics.

The present invention therefore relates, as new product, to a structure-modified GPIR, whose carbohydrate units have been modified by the joint action of periodate ions and of cyanoborohydride ions, the latter reducing into stable primary alcohol groups the aldehyde groups created by the oxidation with periodate, as and when these groups appear. The present invention further relates to the method for preparing the GPIR modified as described hereinabove.

The present invention also relates to products belonging to the class of the immunotoxins, which are obtained by covalent coupling between, on the one hand, an antibody or antibody fragment, used in its natural form or correctly modified, and on the other hand, a molecule of GPIR whose carbohydrate units have been modified as described hereinabove.

Figure 1:
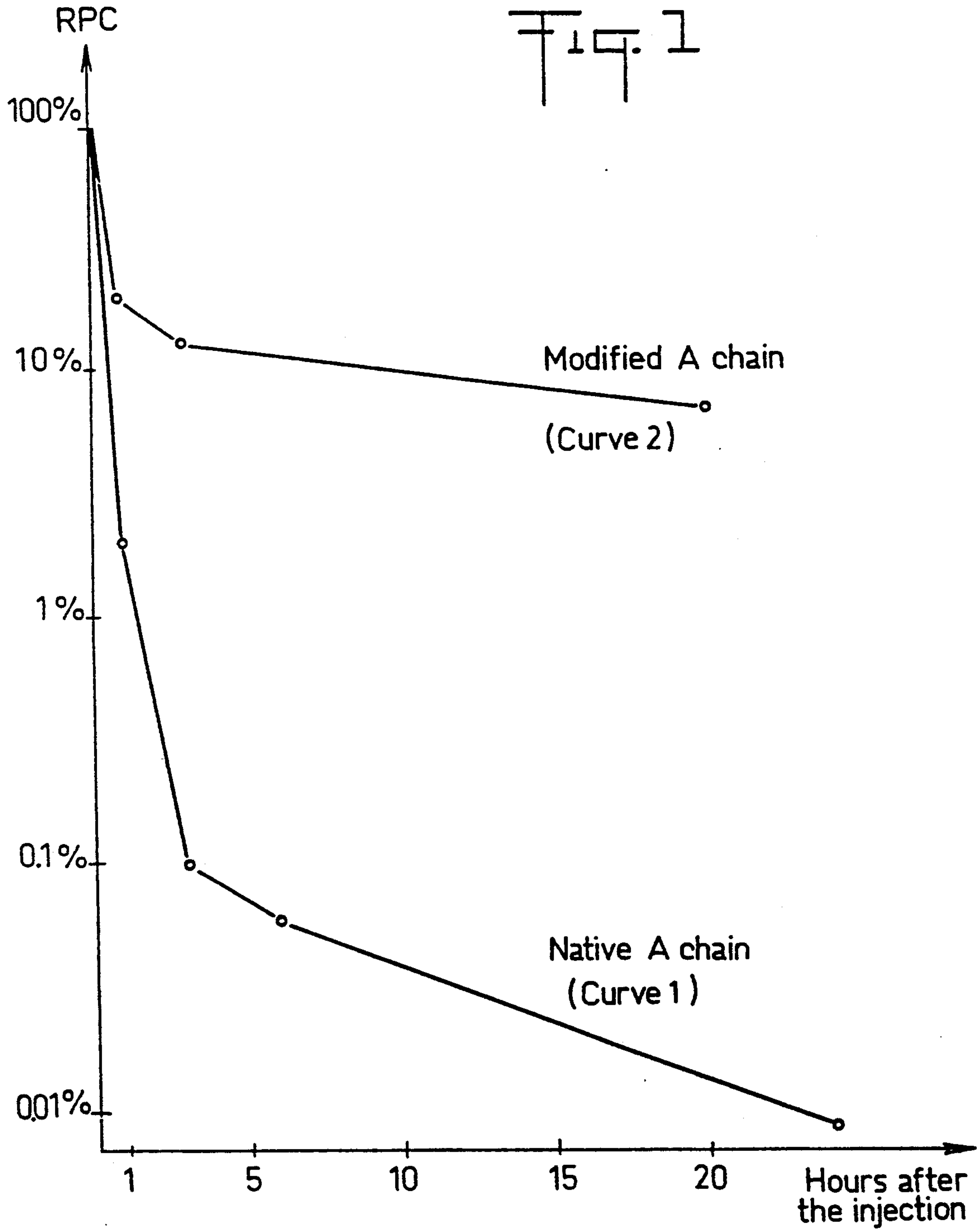
FIG. 1 shows the plasma elimination curves as a function of time for native A chain (curve 1) and a modified A chain (curve 2) according to the present invention.

The meaning is given hereunder of the different products used in carrying out the invention.

The term "periodate" denotes the $IO^{-}_4$ present in aqueous solutions of periodic acid salts and in particular salts deriving from alkaline metals. Said salts are also mentioned in the literature under the name of metaperiodates.

The term "cyanoborohydride" designates the $CNBH^{-}$ ion present in aqueous solutions of cyanoborohydrides and in particular those derived from alkali metals.

The term "antibody" denotes a protein selected from any antibody or antibody fragment, or any immunoglobulin or immunoglobulin fragment or any molecule derived from the above by artificial modification of any one of their functional groups, including osidic structures that they carry, with the proviso that the protein chosen in this way remains capable of selectively recognizing a given antigen on the surface of the cells carrying this antigen, and in particular cancerous cells. The starting antibody may be polyclonal or monoclonal. The starting protein may be of natural or biosynthetic origin, being derived from a cell whose genotype has been modified for this purpose.

The preparation of monoclonal antibodies directed in particular against definite human target cells has been widely covered in the scientific literature and many of these antibodies are now available on the market.

The symbol P represents a protein chosen from the group comprising any antibody or antibody fragment, any immunoglobulin or immunoglobulin fragment or any molecule derived from the above by artificial modification of any one of their functional groups, including carbohydrate structures which they carry, with the proviso that the protein chosen in this way remains capable of selectively recognizing a given antigen on the surface of the cells carrying this antigen, especially the target cells. The starting protein P can be of natural or biosynthetic origin, being derived from a cell whose genotype has been modified for this purpose.

The symbol "GPIR" represents a glycoprotein which inactivates ribosomes or one of its fragments: provided that such fragments retain all or part of the ribosomes inactivating property which characterizes the GPIR from which they are issued, they can also be used as starting products, but the native GPIR is preferred.

The symbol "GPIR-1a" represents the GPIR modified according to the invention, namely a molecule having the property of inactivating ribosomes like the GPIR but having a period of action in vivo which is greater than that of the GPIR and which results from the treatment of the GPIR jointly with an aqueous solution of an oxidizing agent such as a periodate and an aqueous solution of a cyanoborohydride. The operation is generally conducted at a pH of between 5 and 7 in the absence of light and for a period of 0.2 to 24 hours.

In the immunotoxin, the GPIR-1a part is also denoted as a "cytotoxic sub-unit".

The symbol A-1a represents a prolonged-action glycoprotein which inactivates ribosomes, obtained by treatment of the A chain of ricin, in which at least one of the thiol groups of its cysteines 171 and 257 is optionally protected, with an aqueous solution of an alkali metal periodate and a cyanoborohydride, for a period of 0.2 to 24 hours, at a temperature of 0° to 15 ° C. and in the absence of light, and by deprotection of the said thiol group, if appropriate The symbol P′ represents a radical derived from the above protein P, as such or appropriately chemically modified, from which one or more of its own groups have been removed and in which other functional groups are optionally blocked.

The symbol GPIR-1a′ represents a radical derived from the above protein GPIR-1a, as such or appropriately chemically modified, from which one or more of its own groups have been removed and in which other functional groups are optionally blocked.

The symbol A-1a′ represents a radical derived from the protein A-1a, from which at least one of the thiol groups of its cysteines 171 and 257 have been removed.

The symbol $P_1$ represents one of the proteins GPIR-1a and P as defined above, which carries free thiol groups attached to the said protein directly or via a spacing structure.

The symbol $P_2$, which is different from $P_1$, represents one of the proteins GPIR-1a and P as defined above, which carries one or more functional groups capable of reacting with the free thiols.

The symbol $P_{1'}$ represents that radical of the protein $P_1$ which is bonded to the groups belonging to the protein $P_1$, especially the groups SH (of the cysteine), $NH_2$ (in the terminal position of the protein or in the epsilon position of the lysines), OH (of the tyrosines) or COOH (of the aspartic and glutamic acids), or, only in the case where $P_1$ is an antibody or antibody fragment, that radical of the protein $P_1$ which originates from the opening of the carbohydrate structures by reaction with periodic acid according to known methods.

The symbol $P_{2'}$ represents that radical of the protein $P_2$ which is bonded to the characteristic functional groups $NH_2$ (in the terminal position of the protein or in the epsilon position of the lysines), OH (of the tyrosines) or COOH (of the aspartic and glutamic acids).

For example, $P_{1'}$—SH represents the protein $P_1$ (which can arbitrarily be the antibody or antibody fragment P or the protein GPIR-1a) in which the SH groups of the cysteines are free and the other functional groups are optionally blocked.

In the same way, $P_{1'}$—CO— represents the protein $P_1$ in which the terminal carboxyl group or the carboxyl groups of its glutamic and aspartic acids are coupled with a group which artificially introduces an SH group.

Again, $P_{2'}$—NH— represents the protein $P_2$ (which can arbitrarily be the antibody or antibody fragment P or the protein GPIR-1a) in which the terminal amino group or the amino groups of its lysines are attached to a group capable of coupling with the thiol of the protein $P_1$.

The term "inert spacing structure", as used here for E and E′, denotes a divalent organic radical which is inert towards the reactants used in the process, such as a straight-chain or branched alkylene group containing from 1 to 15 carbon atoms, which can contain one or more double bonds, can be interrupted by oxygen atoms or can be substituted by one or more inert functional groups such as methoxy groups, free or esterified carboxyl groups, dialkylamino groups or carbamate groups. The same term also denotes an arylene group containing from 6 to 15 carbon atoms, which can be substituted by one or more inert functional groups as indicated above for the alkylene group.

The expression "functional group capable of bonding covalently", as used here for Y and Y′, denotes any groups capable of reacting with the groups belonging to the proteins $P_1$ and $P_2$ to give a covalent bond. Thus, the groups —CO— and —(C=NH)— are suitable functional groups capable of bonding with the free amines, the thiols and the phenolic hydroxyls of the proteins. Likewise, the —NH— group is a suitable functional group capable of bonding with the free carboxyl groups of the proteins. The group =N— is a suitable functional group capable of bonding with the two carbon atoms of the carbohydrate structures of the proteins $P_1$ and $P_2$ after oxidation with periodate ions, but only in the case where $P_1$ and $P_2$ are an antibody or an antibody fragment.

The expression "group belonging to the proteins", as used here for Z and Z′, denotes the radicals originating from the characteristic groups of the amino acids forming the proteins $P_1$ and $P_2$, such as the oxygen atom originating from the hydroxyls of the tyrosine and possibly serine amino acids, the carbonyl group originating from the terminal carboxyl or the free carboxyls of the aspartic and glutamic acids, the —NH— group originating from the terminal amine of the proteins, for example the lysine, or the sulfur atom originating from the thiol of the cysteine. The same expression also denotes the group originating from the dialdehyde structure obtained after oxidation of one of the carbohydrate structures of the proteins $P_1$ and $P_2$ by treatment with periodate ions, but only in the case where $P_1$ and $P_2$ are an antibody or antibody fragment.

The term "activating radical", as used here for X, denotes a group bonded to an —S—S— bridge and capable of reacting with a free thiol to form a disulfide with the release of X-SH. Suitable activating radicals are pyridin-2-yl and pyridin-4-yl groups which are unsubstituted or substituted by one or more halogens or alkyl, carboxyl or alkoxycarbonyl radicals; the phenyl group which is unsubstituted or, preferably, substituted by one or more halogens or nitro, alkoxy, carboxyl or alkoxycarbonyl groups; or an alkoxycarbonyl group such as methoxycarbonyl.

The terms "alkyl" and "alkoxy" denote groups containing up to 5 carbon atoms.

The term "alkylene" denotes straight-chain or branched saturated aliphatic groups containing up to 10 carbon atoms, which can be substituted by one or more inert functional groups such as alkoxycarbonyl groups.

The glycoproteins which inactivate ribosomes and which are used as starting materials for oxidation with periodate, ions and reduction, according to the invention, are all GPIRs, such as the A chain of ricin, which are in themselves only very slightly cytotoxic because they cannot fix to cells, but which, on the other hand, after coupling with an antibody recognizing particular cells, become highly cytotoxic towards these cells once the antibody has recognized its target.

Representative starting compounds are the A chain of ricin, gelonine and the substance extracted from Momordica charantia (MOM), as obtained by extraction.

Other GPIRs which are useful as starting materials for oxidation with periodate ions are as follows:

| List | |
|---|---|
| Dianthin 30 | from *Dianthus caryophyllus* |
| Dianthin 32 | from *Dianthus caryophyllus* |
| Agrostin A | from *Agrostemma gitnago* |
| Agrostin B | from *Agrostemma gitnago* |
| Agrostin C | from *Agrostemma gitnago* |
| HCI | from *Hura crepitans* |
| *Asparagus officinalis* inhibitor | from *Asparagus officinalis* |

The same substances produced biosynthetically by cells whose genotype has been modified for this purpose are also suitable compounds.

Fragments of the above GPIRs, provided they retain all or part of the property of inactivating ribosomes which characterizes the GPIR from which they are derived, can also be used as starting materials.

The native A chain of ricin in which at least one of the thiol groups is protected is a preferred starting compound.

The preparation of the pure A chain of ricin is described in U.S. Pat. No. 4,340,535. Gelonine and MOM are also described.

Protection of the thiol groups of the starting GPIRs is only necessary if the said thiol groups are those which are to be used for coupling with the antibody. If other functional groups are used for the coupling, for example the phenolic hydroxyl of the tyrosines, or amino groups or carboxylic groups of the GPIR, protection is not carried out.

Blocking is carried out by reaction with a reagent capable of substituting the SH groups with a radical which can subsequently be removed by reduction or thiol/disulfide exchange, for example 2,2'-dinitro-5,5'-dithiodibenzoic acid (DTNB) or alternatively 3-(pyridin-2-yldisulfanyl)propionic acid. In the absence of such a treatment, the free thiols of the A chain may disappear during the oxidation reaction, in which case they cannot be totally regenerated. The excess blocking agent is removed by dialysis or any other suitable treatment.

The GPIR of which the thiols are blocked is then subjected to the oxidation reaction with periodate ions and to the simultaneous reduction reaction of aldehyde groups which have appeared into primary alcohols with the cyanoborohydride ions.

The periodate oxidation reaction and the reduction reaction are carried out at a moderately acid pH, between 5 and 7, and preferably between 6 and 6.5. The periodate is mixed with the cyanoborohydride before the addition of the GPIR. The periodate is used in excess; more particularly, the concentration of alkali metal periodate is always greater than the concentration of the vicinal diols capable of being oxidized; concentrations of 10 to 50 mM in respect of sodium periodate for concentrations of 1 to 10 mg/ml of cytotoxic subunit are suitable. The concentration of the cyanoborohydride is also greater than the concentration of the vicinal diols capable of being oxidized: concentrations of 10 to 200 mM in respect of sodium cyanoborohydride for concentrations of 1 to 10 mg/ml of cytotoxic subunit are suitable. The treatment, carried out at a temperature of between 0° and 15° C. and preferably between 1° and 5° C. and in the absence of light, takes between 0.2 and 24 hours, preferably between 4 and 20 hours.

When the reaction is over, the remaining periodate is removed by the addition of a reagent which consumes it, such as for example an excess of ethylene glycol, or glycerol and the by-products are removed by dialysis or by any other equivalent treatment. The product obtained at the end of the reaction is isolated by the conventional techniques.

If the thiol groups of the starting material have been blocked, unblocking is effected by the known methods, for example by reaction with a reducing agent capable of freeing the previously blocked thiol group, such as 2-mercaptoethanol, giving the new prolongedaction glycoprotein which inactivates ribosomes, ready to be used for coupling with an antibody to give an immunotoxin.

In the case of the A chain of ricin, the new molecule obtained in this way (referred to by the symbol A-1a) possesses the following main properties:

a molecular weight which is not significantly different from that of the native A chain. As far as it is possible to see by polyacrylamide gradient electrophoresis, this modification only produces polymers of the protein in a very small quantity and does not produce any degradation products.

a proportion of free thiol groups greater than 0.7 per mol.

an immunoreactivity towards rabbit antibodies directed against the A chain of ricin which is indistinguishable from that of the native A chain.

an inhibitory activity on protein synthesis in an acellular model which is greater than 50% of that caused by an equal quantity of native A chain.

finally, after a single-intravenous administration to rabbits at a dose of about 0.4 mg/kg of body weight, the plasma level of the prolonged-action A chain (A-1a) present in the bloodstream 24 hours after injection is between 100 and 300 times greater than the plasma level of the native A chain in the same conditions.

A GPIR prepared as described hereinabove, can be used for preparing conjugates or immunotoxins according to the heretofore known methods.

More particularly, the present invention relates to products, belonging to the class of the immunotoxins, (hereinafter named IT) which are obtained by the covalent coupling of, on the one hand, an antibody or antibody fragment, used in its natural form or correctly modified which possesses the capacity to selectively recognize an antigen carried by the intended target cells, with, on the other hand, a prolonged-action glycoprotein GPIR named GPIR-1a, obtained by the process hereinabove disclosed, the coupling of the 2 proteins being effected either via a disulfide bond or via a thioether bond.

An immunotoxin formed by the coupling of an antibody P with a prolonged-action glycoprotein which inactivates ribosomes, GPIR-1a, can be represented by the following statistical formula:

$$P'—W—GPIR—1a' \quad (I)$$

in which P' represents the radical of a protein which is an antibody or an antibody fragment P, as such or appropriately chemically modified, in which other functional groups are optionally blocked, GPIR-1a' represents the radical of a protein which is GPIR-1a, as such or appropriately chemically modified, in which other functional groups are optionally blocked, and W represents a divalent covalent structure containing a thioether group or a disulfide group in which either the sulfur atoms are those of the cysteines of P and GPIR-1a or they are bonded to the groups belonging to P and/or GPIR-1a by spacing structures carrying a functional group bonded to the said groups belonging to P and/or GPIR-1a.

A thioether bond between two proteins is understood as meaning a bond of the type:

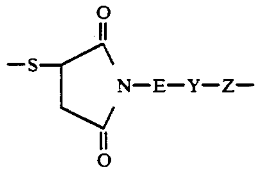

in which Z, Y and E are as defined below.

The present invention preferentially relates to an immunotoxin of the statistical formula:

$$P'—W'—GPIR—1a' \quad (II)$$

in which p' and GPIR-1a' are as defined above and W' represents a covalent structure chosen from:

(a) a group of the formula:

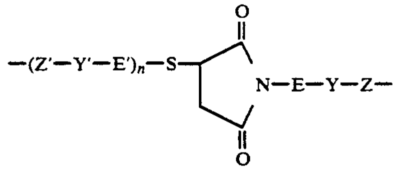

(b) a group of the formula:

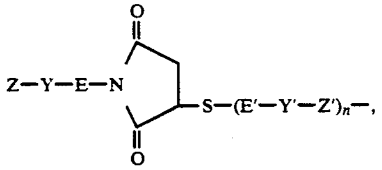

(c) a group of the formula:

$$—Z—Y—E—S—S—(E'—Y'—Z')_n— \text{ or}$$

(d) a group of the formula:

$$—(Z'—Y'—E')_n—S—S—E—Y—Z—,$$

in which:

Z and Z', identical or different, represent the groups belonging to the proteins CPIR-1a and P, chosen from the oxygen atom originating from the hydroxyl of one of the tyrosine residues, the carbonyl group originating from one of the terminal carboxyls or the free carboxyls of the aspartic and/or glutamic acids of GPIR-1a and P, the —NH— group originating from one of the terminal amines of GPIR-1a and P or from one of the amines in the epsilon position of one of the lysine residues, and, only for Z in the covalent structures (b) and (c), the group originating from the dialdehyde structure obtained after oxidation of one of the carbohydrate structures of P with periodic acid according to the known methods;

Y and Y' represent functional groups capable of bonding covalently with any one of the groups Z and Z' of the proteins GPIR-1a and P;

E and E' represent inert spacing structures; and n represents zero or 1.

The immunotoxins of the present invention are represented in simplified form by the formulae I and II above, but it is understood that there can be several structures —W— or —W'— bonded to one and the same molecule P and/or of GPIR-1a, hence of several GPIR-1a bonded to only one P and viceversa; the number of bridges depending on the coupling method and on the numbers of groups belonging to P and to GPIR-1a. Thus statistical formulae I and II also represent these products and their mixtures of formula $$p'(W'—GPIR\text{-}1a')_m$$

in which m is an integer or a mixed number, smaller or greater than 1.

For example, if an immunotoxin is formed by the coupling of the sub-unit A of native ricin with the antibody P (for example the antibody T101) via a divalent covalent structure having a disulfide group in which one sulfur is that belonging to the cysteine 257 of the prolonged-action A chain of ricin and the other is bonded to the phenolic oxygens of the tyrosines of the antibody P by an oxopropyl group, it will have the statistical formula:

$$P'(O—CO—CH_2—CH_2—S—S—A—1a')_t$$

in which t represents the number of tyrosines in the antibody (for example the antibody T101) which are involved in the coupling.

The resulting immunotoxin thus corresponds to a product of the formula II in which:

P' is as defined above, especially the radical of the antibody T101 from which the phenolic groups of the tyrosines involved in the coupling have been removed;

A-1a' is the radical of the prolonged-action A chain of ricin from which the thiol group of its cysteine 257 has been removed; and W' is the group(c):

$$—Z—Y—E—S—S—(E'—Y'—Z')_n—$$

in which Z is the oxygen of the phenolic hydroxyls involved in the coupling, Y is —CO—, E is the inert spacing structure $—CH_2—CH_2—$ and n is zero.

Particular preference is given to the immunotoxins formed by one or more structures containing the prolonged-action sub-unit A of ricin and a single antibody P, which are represented by the statistical formula:

$$P'(W'-A-1a')_m \quad III$$

in which P', W' and A-1a' are as defined above and m represents the number of groups belonging to the protein p which are involved in the coupling. The number m varies from 0.3 to 12, preferably from 0.5 to 10.

The expression "m varies from 0.3 to 12, preferably from 0.5 to 10" means that the value of m is a statistical value because the coupling does not take place homogeneously within the population of antibody molecules. The number m may therefore not be an integer.

The value of m depends especially on the antibodies used and more particularly on their molecular weight.

Thus, if a fragment Fab or Fab' is used as the starting antibody P, the value of m can vary between 0.3 and about 2; if a fragment $F(ab')_2$ is used, m can vary between 0.5 and about 4; for an antibody of the IgG type, the value of m will be between 0.5 and about 6; finally, for an antibody IgM, the value of m can vary between 1 and about 12.

It is preferable, however, for the degree of substitution on the antibody P to be such as to lead to a value of m which is not less than 0.5 and not more than 10.

More generally, the structures 1 and 11 above represent statistical formulae written in simplified form, as explained above.

Analogously, the formulae IV, V and IX below are also statistical formulae—whenever n is 1—because the coupling reactants are prepared from populations of proteins $P_1$ and $P_2$ which all have exactly the same properties as those considered above for the antibody P, whether these proteins $P_1$ and $P_2$ are themselves the antibody P or the protein GPIR-1a.

According to another feature, the present invention relates to a process for the preparation of a prolonged-action immunotoxin having a covalent bond of the disulfide or thioether type between an antibody and a glycoprotein which inactivates ribosomes, wherein a disulfide or thioether bond is formed between an antibody and a prolonged-action glycoprotein which inactivates ribosomes, obtained by treatment of a glycoprotein which inactivates ribosomes, the thiol groups of which are optionally protected, with an aqueous solution of an alkali metal periodate, in the presence of a cyanoborhydride for a period of 0.2 to 24 hours, at a temperature of 0° to 15° C. and in the absence of light, and by unblocking of the thiol group, if appropriate.

According to a preferred feature, the present invention relates to a process for the preparation of an immunotoxin having the structure 1 above, wherein a protein $P_1$, which is arbitrarily either the prolonged-action glycoprotein which inactivates ribosomes, CPIR-1a, or an antibody or antibody fragment, carrying at least one free thiol group attached to the said protein $P_1$ directly or via a spacing structure, is reacted, in aqueous solution and at room temperature, with a protein $P_2$, which is different from $P_1$ and is arbitrarily either the prolonged-action glycoprotein which inactivates ribosomes, GPIR-1a, or an antibody or antibody fragment, carrying a group capable of coupling with the free thiol of the protein $P_1$, so as to form a thioether or disulfide bond.

According to a particularly advantageous feature, the present invention relates to a process for the preparation of an immunotoxin having the structure II, in which P', W' and GPIR-1a' are as defined above, wherein a protein of the formula:

$$P_{1'}-(Z-Y-E)_n-SH \quad (IV)$$

is reacted, in aqueous solution and at room temperature, with a protein of the statistical formula:

$$P_{2'}-Z'-Y'-E'-G \quad (V)$$

in which $P_1$, and $P_2$, represent the radicals of the proteins $P_1$ and $P_2$ bonded to the groups belonging to the said proteins, or, only if $P_1$ and $P_2$ are an antibody or antibody fraction, the radicals of the proteins $P_1$ and $P_2$ originating from the opening of the carbohydrate structures by reaction with periodic acid, Z, Z', Y, Y', E and E' are as defined above and G represents a group:

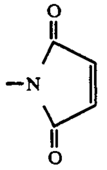

or a group —S—S—X, in which X is an activating group.

Therefore, both P and GPIR-1a are proteins which arbitrarily have:

(1) the thiol group or groups taking part in the coupling, and (2) one or more functional groups capable of reacting with the above thiol groups to form a disulfide or thioether bond.

According to the present invention, the said thiol groups and functional groups are those of the native proteins P or GPIR-1a or alternatively are introduced therein artificially.

Protection of the thiol groups of the starting GPIRs is only necessary if the said thiol groups are those which are to be used for coupling with the antibody. If other functional groups are used for the coupling, for example the phenolic hydroxyl of the tyrosines, protection is not carried out.

Blocking is carried out by reaction with a reagent capable of substituting the SH groups with a radical which can subsequently be removed by reduction or thiol/disulfide exchange, for example 2,2'-dinitro-5,5'-dithiodibenzoic acid (DTNB) or alternatively 3-(pyridin-2-yldisulfanyl)propionic acid. In the absence of such a treatment, the free thiols of the A chain may disappear during the oxidation and reduction reaction, in which case they cannot be totally regenerated by reaction with a reducing agent such as 2-mercaptoethanol. The excess blocking agent is removed by dialysis.

The glycoprotein which inactivates ribosomes and the thiols of which are blocked is then subjected to oxidation with periodate ions and to reduction. If, on the other hand, the cytotoxic sub-unit does not contain thiol, or alternatively if the thiol or thiols are not used for coupling, the blocking indicated above is not carried out.

The preparation of the conjugates or immunotoxins from the prolonged-action glycoproteins which inactivate ribosomes is carried out by any process suitably chosen from the range of processes described in U.S. Pat. No. 4,340,535. If the chosen cytotoxic sub-unit naturally contains at least one thiol making it suitable for coupling, this group will preferably be used by reaction with the antibody or antibody fragment carrying an activated disulfide group. If the chosen cytotoxic sub-unit does not naturally possess a thiol group making it suitable for coupling, at least one functional group carrying a free thiol can preferably be introduced artificially into the said sub-unit, after the oxidation step with periodate ions and reduction, by any known process and the coupling can be continued as indicated above.

The introduction of the said functional group can take place either before the oxidation step with periodate ions, and the reduction steps, in which case it will be necessary for the thiol radical to be blocked during the oxidation and reduction step and then unblocked after this step, i.e. the oxidation and reduction step.

The chemical coupling of the GPIR-1a with the antibody (or antibody fragment) can be effected according to the process of the present invention by procedures which:

preserve the respective biological activities of the two components of the conjugate, namely the antibody and the GPIR-1a, ensure that the process has a satisfactory reproducibility and a good coupling yield, make it possible to control the value of the ratio GPIR-1a/antibody in the conjugate obtained, lead to a stable and water-soluble product.

Among the procedures corresponding to these characteristics, preference must be given to those which involve one or more thiol groups in forming the bond between the 2 proteins. In fact, these thiol groups are particularly suitable for forming either disulfide bonds or thioether bonds, both of which satisfy the general conditions above.

The preparation of immunotoxins simultaneously having the following characteristics:

the covalent bond between the A chain of ricin and the antibody contains a disulfide radical, one of the sulfur atoms forming the disulfide bond is always the sulfur atom belonging to the cysteine residue in the 257-position of the A chain of ricin, and the link joining the A chain of ricin to the antibody is fixed to the latter at $NH_2$ side groups or end groups of a peptide chain The coupling of an antibody with the A chain of ricin is described in detail in U.S. Pat. No. 4,340,535.

The same method can be applied to the preparation of immunotoxins having the same characteristics and formed by the coupling of an antibody or antibody fragment with a GPIR-1a.

The preparation of immunotoxins formed by the coupling of an antibody or antibody fragment with a GPIR-1a and by a covalent bond of the disulfide or thioether type at different functional groups is described in detail below.

In general, in order to carry out the coupling reactions between proteins successfully and to eliminate disordered crosslinkings in particular, it is important for one of the proteins to be coupled, and one only, to carry the thiol or thiol groups to be used, while the other protein only carries one or more groups capable of reacting with the thiols in an aqueous medium having a pH of between 5 and 9, and at a temperature not exceeding 30° C., to produce a stable and clearly defined covalent bond.

The characteristics of the proteins $P_1$ and $P_2$ used as starting materials are illustrated in detail below. The spacing structure E can be replaced with the preferred structures R to $R_8$, which are only given as examples.

I—THE PROTEIN $P_1$

As this protein is in all cases the one carrying the thiol group or groups which will take part in the coupling, the situation which arises varies according to the nature of this protein $P_1$.

A) In the natural state, the protein $P_1$ carries one or more thiol radicals which can be used to permit coupling with the protein $P_2$; this is particularly the case if the protein $P_1$ is the antibody fragment known as F(ab)', as conventionally obtained by limited proteolysis of the antibody in the presence of pepsin, followed by reduction of the disulfide bridge (or bridges) between high-molecular chains.

This is also the case if the protein $P_1$ is a GPIR-1a, for example the modified A chain of ricin (A-1a), or a derivative thereof, in which at least one of the thiol groups carried by the cysteine 171 and 257 residues of the native A chain of ricin is free and accessible for chemical coupling.

In all these cases, the protein $P_1$ carrying its natural thiol group (or groups) can be used in this state for the coupling step.

B) In the natural state, the protein $P_1$ does not carry thiol radicals which can be used to permit coupling with the protein $P_2$:

this is especially the case if the protein $P_1$ is a native immunoglobulin, a whole antibody or an antibody fragment, especially one of the fragments conventionally called $F(ab)'_2$ or F(ab);

another case in which the protein $P_1$ does not carry, in the natural state, a thiol group which can be used for coupling is the case where this protein $P_1$ is a GPIR-1a, for example the prolonged-action A chain of ricin, in which each of the two cysteine residues is either blocked by alkylation or inaccessible for chemical modification.

In all cases, it will thus be appropriate artificially to introduce into such molecules one or more thiol groups capable of permitting coupling.

Three types of reaction can preferably be used for the introduction of thiol groups:

1—The first type of reaction is with S-acetylmercaptosuccinic anhydride, which is capable of acylating amino groups of the protein. It will then be possible to free the thiol groups by reaction with hydroxylamine to remove the acetyl protecting radical, in the manner already described (Archives of Biochemistry and Biophysics, 119, 41–49, 1967). It will even be possible, in the case where the thiol group (or groups) thus introduced in the protected form are subsequently to react with an activated mixed disulfide radical, to dispense with the prior deprotection by means of hydroxylamine; in fact, the reaction creating the disulfide bond using the reactants forming the subject of the present invention takes place just as well with the S-acetyl radical as with the free thiol.

Other methods described in the scientific literature can also be used to introduce thiol groups into the protein to be modified.

2—The second type of reaction consists in reacting the protein via its carboxyl groups with a symmetrical diamino molecule having a disulfide bridge, of the formula:

$$H_2N—R_1—S—S—R_1—NH_2$$

in which $R_1$ is an aliphatic group containing from 2 to 5 carbon atoms.

The reaction is preferably carried out with cystamine [$R_1$=—$(CH_2)_2$—] in the presence of a coupling agent such as a carbodiimide and especially a watersoluble derivative like 1-ethyl-3-dimethylaminopropyl-3-carbodiimide, and leads to the formation, depending on the stoichiometries used, of one of the following derivatives or a mixture of both:

$$P_{1'}—CO—NH—R_1—S—S—R_1—NH_2 \quad (Ia)$$

$$P_{1'}—CO—NH—R_1—S—S—R_1—NH—CO—P_{1'} \quad (Ib).$$

A reaction product of this type can then be used in two ways:

a) If, in the formulae Ia or Ib, the protein $P_1$ is a GPIR-1a, for example the prolonged-action A chain of ricin or one of its derivatives, the reaction medium obtained is subjected, without fractionation, to the action of a reducing agent such as 2-mercaptoethanol, giving a single protein derivative of the general formula:

$$P_{1'}—CONH—R_1—SH.$$

The product thus obtained is then purified by dialysis or gel filtration.

b) If, in the formulae Ia and Ib, the protein $P_1$ is an antibody or one of its fragments, the reaction medium obtained will be used as such for the coupling, in which case a thiol/disulfide exchange method will be used, for example the one described by Gilliland and Collier (Cancer Research, 40, 3564, 1980).

3—The third type of reaction consists in using carbohydrate units, which are present in the natural state in the antibodies, in order to fix the radical carrying the thiol which it is proposed to introduce. The protein $P_1$ is then subjected to oxidation with periodate ions by the known methods in order to create aldehyde groups on the carbohydrate units. After the reaction has been stopped by the addition of excess ethylene glycol and the by-products and excess reactants have been removed by dialysis, the product obtained is treated with a symmetrical diamino molecule having a disulfide bridge, of the general formula:

$$H_2N—R_1—S—S\text{-}R_1—NH_2$$

in which $R_1$ is an aliphatic group containing from 2 to 5 carbon atoms. The formed addition products are then reduced in secondary or tertiary amines by the action of a suitable metal hydride, notably the sodium borohydride. The reaction is preferably carried out with cystamine [$R_1$=—$(CH_2)_2$—] and leads to the formation, depending on the stoichiometries used, of one of the following derivatives or a mixture of both:

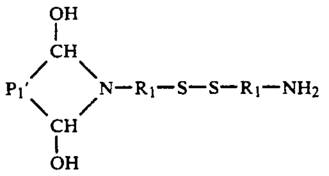

IIa

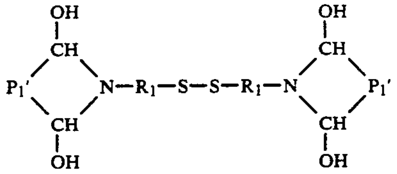

IIb

The reaction medium obtained may then be treated exactly as indicated above for the products characterized by the structures Ia or Ib.

In the last two types of reaction, described above, for the artificial introduction of thiol groups (the types using a symmetrical diamino disulfide reactant), the protein $P_1$ used preferably possesses neither free SH groups nor free amino groups.

In the case of the GPIR-1a, this can always be achieved by alkylation of the natural SH group or groups by reaction with a customary reagent for thiols, such as N-ethylmaleimide or iodoacetic acid or one of its derivatives, and by methylation of the natural $NH_2$ groups in accordance with the reductive methylation process described by MEANS and FEENEY (Biochemistry 7, 2192 (1968)). For example, up to 6 methyl radicals per mol can be introduced beforehand into the modified native A chain of ricin. A protein of this type retains all its biological properties and especially its capacity to inhibit ribosomal protein synthesis in eucaryotic cells.

In the cases of antibodies or antibody fragments and, more generally, all the substances of the first group, as defined previously, which do not possess naturally free SH groups, it will be appropriate to carry out a reductive methylation, for example by the method of MEANS and FEENEY; in this way, it is usually possible to introduce several dozen methyl radicals per mol of antibody without modifying its capacity to selectively recognize an antigen on the surface of the cells carrying this antigen.

II—THE PROTEIN $P_2$

This protein is in all cases the one which carries one or more functional groups capable of reacting with the thiols of the protein $P_1$ to form either a disulfide or a thioether bond. These functional groups, which are always introduced artificially into the protein $P_2$, differ according to whether it is desired to effect coupling by a disulfide bond or by a thioether bond and are chosen as indicated below.

1) The disulfide bond

In this case, the preparation of the conjugate can be represented by the equation:

$$P_{1'}—(Z—Y—E)_n—SH + P_{2'}—Z'—Y'—E'—S—S—X \rightarrow P_{1'}—(Z—Y—E)_n—S—S—E'—Y'—Z'—P_{2'} + X—SH$$

The protein $P_2$ substituted by an activated sulfur atom is obtained from the protein $P_2$ itself or from the correctly protected protein $P_2$ by substitution with a reagent which itself carries an activated sulfur atom, according to the equation:

$P_2 + L—Y'—R—S—S—X \rightarrow P_{2'}—Z'—Y'13$
$R'—S—S—X$ in which:

$P_2$ denotes the protein to be substituted and

L—Y' represents a group permitting the covalent fixation of the reagent to the protein.

The functional group L—Y' is a group capable of bonding covalently with any one of the groups carried by the side chains of the constituent amino acids of the protein to be substituted. Among these groups, the following may be singled out in particular:

a) The amino end groups of the peptide chains or the amino side groups of the lysyl radicals contained in the protein. In this case, L—Y' can represent especially:

a carboxyl group which can bond to the amino groups of the protein in the presence of a coupling agent such as a carbodiimide and especially a water-soluble derivative like 1-ethyl-3-dimethylaminopropyl-3-carbodiimide; 3-(2-pyridyldisulfanyl)propionic acid activated by the above mentioned carbodiimide may be used for this purpose.

a carboxylic acid chloride which is capable of reacting directly with the amino groups to acylate them;

a so called "activated" ester such as an ortho- or para-nitrophenyl or -dinitrophenyl ester, or alternatively an N-hydroxysuccinimide ester, which can react directly with the amino groups to acylate them such as the N-succinimidy-3-(2-pyridyl-dithio) propionate an internal anhydride of a dicarboxylic acid, such as, for example, succinic anhydride, which reacts spontaneously with the amine groups to create amide bonds; or an imidoester group:

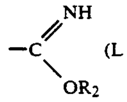 (L = $OR_2$, Y' = —(C=NH)—)

in which R is an alkyl group, which reacts with the amino groups of the protein $P_2$ according to the equation:

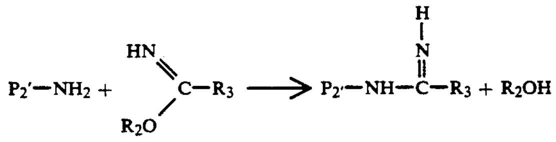

in which $R_3$ represents the group —R—S—SX;

b) the phenol groups of the tyrosyl radicals contained in the protein. In this case, L—Y' can represent especially an imidazol-1-ylcarbonyl group, which reacts with the phenol groups of the protein according to the equation:

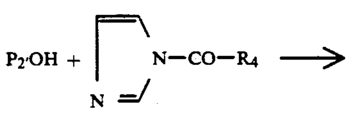

-continued

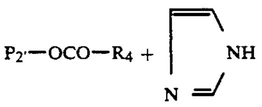

in which the imidazol-1-yl is L, the CO group is Y' and $R_4$ is the group —R—S—S—X.

The radical —S—S—X denotes an activated mixed disulfide capable of reacting with a free thiol radical. In particular, in this mixed disulfide, X can denote a pyridin-2-yl or pyridin-4-yl group optionally substituted by one or more alkyl, halogen or carboxyl radicals. X can also denote a phenyl group preferably substituted by one or more nitro or carboxyl groups. Alternatively, X can represent an alkoxycarbonyl group such as the methoxycarbonyl group.

The radical R denotes the spacing structure (indicated as E in the general formula 11 above) capable of carrying the substituents Y' and S—S—X simultaneously. It must be chosen so as not to contain groups capable of interfering, during the subsequent reactions, with the reactants used and the products synthesized. In particular, the group R can be a group $—(CH_2)_n—$, n being between 1 and 10, or alternatively a group:

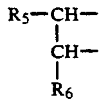

in which $R_6$ denotes hydrogen or an alkyl group having from 1 to 8 carbon atoms and $R_5$ denotes a substituent which is inert towards the reactants to be used subsequently, such as a carbamate group:

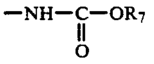

in which $R_7$ denotes a linear or branched alkyl group having from 1 to 5 carbon atoms, especially the tert.butyl group. The reaction of the compound L—Y'—R—S—S—X with the protein $P_2$ is carried out in a homogeneous liquid phase, most commonly in water or a buffer solution. If necessitated by the solubility of the reactants, a water-miscible organic solvent can be added to the reaction medium at a final concentration which can reach 20% by volume in the case of a tertiary alcohol, such as tertiary butanol, or 10% by volume in the case of dimethylformamide or tetrahydrofuran.

The reaction is carried out at room temperature for a period of time varying from a few minutes to a few hours, after which the low molecular weight products, and in particular the excess reactants, can be removed by dialysis or gel filtration. This process usually makes it possible to introduce between 1 and 15 substituent groups per mol of protein.

When using such compounds, the coupling with the protein $P_1$ is carried out by bringing the two proteins together in an aqueous solution having a pH of between 6 and 8, at a temperature not exceeding 30° C., for a period of time varying from 1 hour to 24 hours. The aqueous solution obtained is dialyzed, if appropriate, to remove the low molecular weight products, and the conjugate can then be purified by a variety of known methods.

2) The thioether bond

In this case, the preparation of the conjugate consists in reacting $P_{1'}$—(Z—Y—E)$_n$—SH with the protein $P_2$ into which one or more maleimide radicals have been introduced beforehand.

The reaction is then represented by the following equation, which is given as an example:

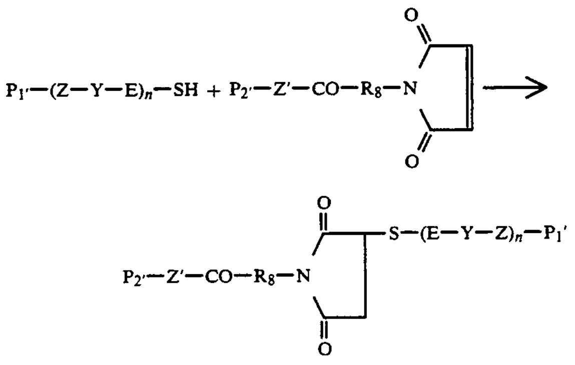

in which:

$R_8$ represents an aliphatic or aromatic spacing structure containing from 1 to 15 carbon atoms, which is inert towards the reactants to be used subsequently, and Z' represents groups which can vary according to the type of functional group substituted on the protein $P_2$.

Thus, Z'=oxygen in the case of an ester on the phenol of a tyrosyl residue, Z=NH in the case of the coupling of an activated carboxyl group with an amino group of the protein, or Z'=NH—$CH_2$ in the case of the reaction of a chloromethyl ketone with an amino group of the protein.

The protein $P_2$ substituted by the maleimide group or groups is obtained from the protein $P_2$ itself, or the correctly protected protein $P_2$, by substitution of suitable groups of the protein with a reagent which itself carries the maleimide group. Among these suitable groups, the following may be singled out in particular:

a) The amino end groups of the peptide chains or the amino side groups of the lysyl residues contained in the protein. In this case, the reagent carrying the maleimide radical can be:

either a reagent of the general formula:

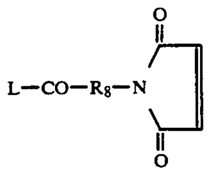

in which L—CO— represents:

either a carboxyl group, in which case the reaction is carried out, after activation of the carboxyl group, in the presence of a coupling agent such as a carbodiimide and especially a water-soluble derivative such as 1-ethyl-3-dimethylaminopropyl-3-carbodiimide, or a so-called "activated" ester such as an ortho- or para-nitrophenyl or -dinitrophenyl ester, or alternatively an N-hydroxysuccinimide ester, which reacts directly with the amino groups to acylate them.

The preparation of such reagents is described especially in Helvetica Chimica Acta 58, 531-541 (1975). Other reagents in the same class are commercially available.

or a reagent of the general formula:

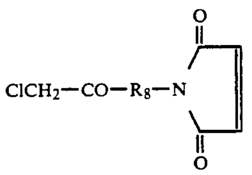

which is capable of reacting with the amino groups of the protein $P_2$ according to the equation:

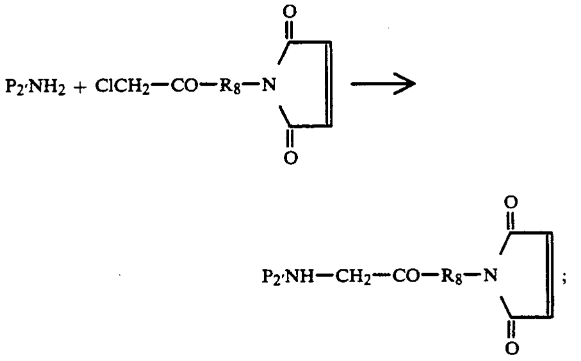

b) the phenol groups of the tyrosyl radicals contained in the protein. In this case, the reagent carrying the maleimide radical can be a reagent of the general formula:

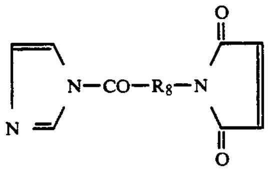

which reacts with the phenol groups of the protein according to the equation:

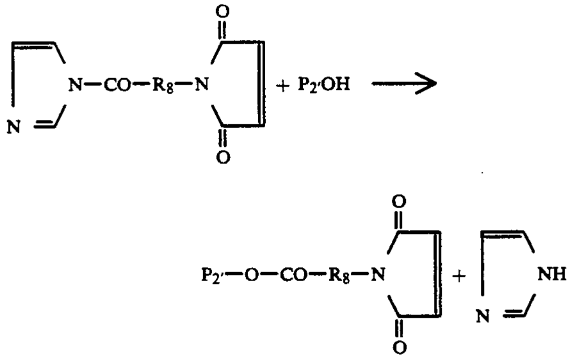

The reaction of the maleimide-carrying reagents with the protein $P_2$ is carried out in a homogeneous liquid phase, most commonly in water or a buffer solution. If necessitated by the solubility of the reactants, a water-miscible organic solvent can be added to the reaction medium at a final concentration which can reach 20% by volume in the case of a tertiary alcohol, such as tertiary butanol, or 10% by volume in the case of dimethylformamide or tetrahydrofuran.

The reaction is carried out at room temperature for a period of time varying from a few minutes to a few hours, after which the low molecular weight products, and in particular the excess reactants, can be removed by dialysis or gel filtration. This process usually makes it possible to introduce between 1 and 15 substituent groups per mol of protein.

When using such compounds, the coupling with the protein $P_1$ is carried out by bringing the two proteins together in an aqueous solution having a pH of between 6 and 8, at a temperature not exceeding 30° C., for a period of time varying from 1 hour to 24 hours. The solution obtained is dialyzed, if appropriate, to remove the low molecular weight products, and the conjugate can then be purified by a variety of known methods.

The compounds of the formula:

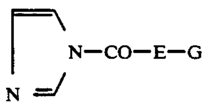

VI in which E and G are as defined above, are prepared by a process which comprises reacting a compound of the formula:

G—E—COOH VII in which G and E are as defined above, with the carbonyldiimidazole of the formula:

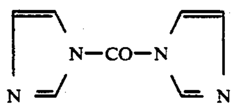

VIII in an organic solvent at a temperature of 10° to 40° C.

The compounds of the formula VI are particularly useful as agents for coupling with the hydroxyls of the tyrosines of the proteins GPIR-1a and P.

According to another feature, the present invention relates to new products having the following statistical formula:

$GP_1$ R-1a"—O—CO—E—G IX in which:

GPIR-1a" represents the radical of the protein GPIR-1a or any molecule derived from the said GPIR-1a by artificial modification of any one of its functional groups, from which one or more phenolic hydroxyl groups of the tyrosines have been removed;

the oxygen atom is that belonging to the phenolic hydroxyl groups missing from the radical GPIR-1a";

and

E and G are as defined above.

Particular preference is given to the compounds of the formula IX in which E represents a group $—(CH_2)_p—$, in which p is an integer from 2 to 7, or a group:

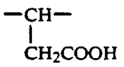

and G is a group of the structure —S—S—X, in which X is an activating radical chosen from the pyridin-2-yl and pyridin-4-yl groups which are unsubstituted or substituted by one or more halogens or alkyl, carboxyl or alkoxycarbonyl radicals, the phenyl group which is unsubstituted or substituted by one or more halogens or nitro, alkoxy, carboxyl or alkoxycarbonyl groups, or an alkoxycarbonyl group.

The products of the formula IX are prepared by reacting a product of the formula:

GPIR-1a"—OH in which GPIR-1a" is as defined above and the hydroxyl group is the phenolic hydroxyl missing from the tyrosines of the radical GPIR-1a", with a compound of the formula VI above, at a temperature of 10° to 40° C., in an aqueous solvent optionally containing a water-miscible organic solvent such as, for example, an ether solvent like dioxane or tetrahydrofuran.

In the case where GPIR-1a is the prolonged-action A chain of ricin, the properties of the resulting immunotoxins IT (A-1a) are as follows:

the average degree of coupling, expressed as the number of mol of modified A chain per mol of antibody, is usually between 0.5 and 5 and in particular between 1 and 3, the separation of the IT (A-1a) by polyacrylamide gel electrophoresis results in a splitting of the product into a series of bands corresponding to products whose molecular weights differ from that of the antibody by successive increments of 30,000 daltons, the studies performed by cytofluorometry make it possible to show that the antibody has not undergone any substantial degradation during the activation and coupling reactions to which it has been subjected, and that it is still capable, within the conjugate itself, of recognizing the antigen against which it is directed, and the inhibitory activity of the A chain, modified and coupled with an antibody, on protein synthesis, determined in an acellular model in the presence of 2-mercaptoethanol, is totally retained.

The cytotoxic activity of the immunotoxins with A-1a chain measured in a test for protein synthesis in a cell model on the cells having the target antigen, is more than 100 times greater than that measured under the same conditions on cells not having the target antigen. For example, the immunotoxin (denoted by IT (A-1a)-AT15E built up by coupling the modified A chain of ricin, by means of a link containing a disulfide bridge, with a monoclonal antibody (denoted by antibody AT15E) directed against the antigen Thy 1.2 present on the surface of certain mice leukemia cells is about 1000 times more cytotoxic towards the positive Thy.1.2 cells than towards the negative Thy 1.2 cells. Moreover, the activity of IT (A-1a) AT15E is identical to that obtained with IT prepared from the same antibody AT15E and the native chain. Finally, after intravenous administration of IT (A-1a) to rabbits at a dose of the order of 0.4 mg/kg of body weight, expressed as A chain, the plasma level of IT (A-1a) present in the bloodstream 24 hours after injection is 50 to 100 times greater than the plasma level of the conventional IT measured under the same conditions. Thus, in a typical case involving rabbits, it is found that the plasma level of IT (A-1a) AT15E in the bloodstream 24 hours after injection is 9% of the product present at time zero, as against 0.08% for the corresponding conventional IT AT15E with non-modified A chain, after the same time, i.e. an increase by a factor of the order of 110.

This gives modified immunotoxins which have acquired a new character as regards their pharmacokinetic properties.

More particularly, by appropriate modification of the cytotoxic sub-unit, it has been possible to add to the specific cytotoxicity properties of immunotoxins, without interfering with them, a new property which is just as intrinsic, namely the capacity to show slow plasma elimination kinetics after injection to superior animals or humans.

Reports have been recently published on works conducted for improving the pharmacokinetic properties of ricin and potentially those of the antibodies-ricin conjugates and of the antibodies-A chain of ricin conjugates. These publications are:

European Journal of Biochemistry (1985), 147, 198-206

Biochemica Biophysica Acta (1985), 842, 12-21,

Cancer Drug Delivery (1985), 3, 191-198.

As explained hereinafter, a detailed examination of these publications has revealed major differences both regarding methodology and regarding the results between these works and the works of the Applicant, wherefrom it is obvious that the products according to the present invention are very superior.

A) Regarding methodology

According to said prior art, the method used for reducing the speed of elimination in vivo of the ricin and potentially that of the antibody-ricin conjugates and of the antibody-A chain of ricin conjugates, has consisted in modifying the osidic units of the whole ricin toxin with a mixture of sodium metaperiodate and sodium cyanoborohydride at pH 3.5 for short periods of time, the longest being one hour.

The process developed by the Applicants differs from the above method by the following points:

1) the modification takes place exclusively on the molecule of purified A chain of ricin ;
2) the reaction pH is much higher (close to neutrality);
3) the optimum duration of the treatment is much longer (between 4 and 20 hours).

It should also be noted that, when the method described in said publications is applied directly to the A chain of purified ricin, the latter is rapidly and irreversibly, nearly completely denaturated, which makes it improper for any subsequent use. This point has been experimentally established by the Applicant. Therefore, the method described in said publications for the whole ricin, is not directly applicable to the molecule of A chain of ricin, so that, the original process for modifying the A chain, discovered by the Applicant is not in any way anticipated by said publications.

B) Regarding the results:

a) Properties of the modified ricin:

The ricin toxin modified according to the method described in said publications has the following essential properties:

the biological activity in vitro of the modified ricin namely its cytotoxic power towards culture cells, is very strongly altered by the treatment, the loss of activity can reach up to 90%.

The overall toxicity in vivo of modified ricin, tested in two species of animals (mice and rats) is, on the contrary, increased by a factor varying between 3 and 4.

It will be noted that these two properties should confer to a conjugate, obtained by coupling an antibody with the ricin modified in that way, properties that are the opposite of what should be expected in immunotoxins, namely the highest cytotoxic power possible towards target cells and the lowest possible toxicity.

The hepatic uptake of ricin which is the major phenomenon responsible for its elimination from the bloodstream is reduced by a factor 2 when the ricin has been modified. The result is an increase in plasma concentration of the modified ricin of a factor equal to 2.3 only with respect to the same concentration when the ricin has not been modified.

It will be further noted that the degree of inhibition of the hepatic uptake of ricin obtained by the chemical modification of its osidic units is less than that obtained when native ricin is co-administered in vivo with an excess of ovalbumin, a glycoprotein which, by its osidic units with terminal mannose, is a powerful competitor of ricin towards receptors of glycoproteins with terminal mannose of the hepatic cells. This indicates that the treatment of ricin such as described in these publications is very inadequate ensure complete destruction of the sugars of ricin which are responsible for the hepatic uptake of toxin.

b) Biological properties of A chain immunotoxins issued from modified ricin

The authors of the above-referred publications have built an immunotoxin by using the A chain of ricin purified from modified ricin. The modified ricin was obtained by treatment of native ricin with sodium periodate and sodium cyanoborohydride at pH 3.5 for 60 minutes. According to the authors, these conditions are the optimum conditions given the best compromise between an increase of the plasma rate of ricin and a decrease of its biological activity (according to these conditions of treatment, the plasma rate of the so-modified ricin is increased by a factor of 2 to 2.3, whereas its activity is reduced by a factor of 4.7).

The A chain issued from such modified ricin was coupled by means of a disulfide bridge to an antibody directed against certain cancerous cells. The studies on the biological properties of said immunotoxin, reported in said publications reveal a considerably reduced activity. The cytotoxicity induced by this conjugate towards the target cells is less by a factor of 3 to 4 than that of the same conjugate built with the A chain of native ricin, this implying that the treatment of the ricin such as described by said authors, which is detrimental to the biological activity of ricin, is also detrimental to the immunotoxins built with the A chain issued from said modified ricin.

A fact to be remembered is that, on the contrary, the immunotoxins with A-1a chain prepared according to the process of the present application, exhibit cytotoxic activities towards target cells, which are identical to that obtained with the same homolog immunotoxins built with the A chain of native ricin.

c) Pharmacokinetic properties of the A chain issued from modified ricin and pharmacokinetic properties of the corresponding immunotoxins From the results reported hereinabove, the authors of said publications expect that the immunotoxins prepared with the A chain issued from the ricin modified according to their method, should have improved pharmacokinetic properties, namely a slower speed of elimination from the blood compartment, thereby increasing their biological properties. However, no experiment results have really proved this essential point. Moreover, such conclusion cannot even be drawn from the published information for the following reasons:

The only results of pharmacokinetics which are given are those obtained experimentally with the whole toxins (ricin and modified ricin) and not with the corresponding A chains. Yet, the ricin toxin contains an oligosaccharidic unit on the B chain. These osidic units, being all with terminal mannose, are also susceptible to be recognized by the nonparenchymal cells carrying receptors capable of recognizing said oses. In practice, it is not known whether the osidic units involved in the ricin elimination process are those carried by the A chains or the B chains or both. It is therefore impossible to know whether the osidic units responsible for the rapid elimination of the A chain, as explained by the Applicant, are the same as those which are also involved in the elimination of ricin.

Consequently, the partial inhibiting of the hepatic uptake of the ricin modified by the process described in the above-cited publications, which proves that the osidic units involved in said process applied to the whole ricin, have been partly modified, does not in any way indicate that the modification of the osidic units of the A chain obtained when working on the whole ricin, is appropriate to ensure an inhibition of the hepatic uptake of the isolated A chain, hence a slow elimination thereof and of the corresponding immunotoxins.

The applicant has then undertaken certain works to determine the pharmacokinetic properties of the A chain isolated from ricin modified according to the method described in the above-cited publications and of the corresponding immuno-toxins. The experimental procedures followed for 1) the modification of ricin, 2) the isolation of the A chain, 3) the coupling of said A chain with the antibody, are strictly identical to those described in said publications, and in publications cited in reference therein.

The results obtained with the A chain issued from ricin modified according to the process described in said publications are compiled in Table I, which also gives, for comparative purposes, the results obtained with the native A chain and with the A-1a chain prepared according to the present invention.

TABLE I

| | Native A chain | A chain issued from modified ricin | A-1a chain |
|---|---|---|---|
| Inhibition of protein synthesis in acellular model (CI50) | $10^{-10}$M | $10^{-9}$M | 1.2 $10^{-10}$M |
| Free thiol per mole of A chain | 0.9 | 0.77 | 0.79 |
| Molecular weight ±3,000 | 30,000 | 30,000 | 30,000 |
| Relative plasma concentration (%) 24 h after the injection | 0.015 | 0.04 | 5 |

Thus, said results show that the A chain of modified ricin exhibits properties that are identical to those of the A-1a chain as regards the number of free thiols per mole of A chain and the molecular weight. On the contrary, these two products differ considerably as far as their biological properties are concerned:

1) the intrinsic biological activity of the A chain, which is its power to inhibit the protein synthesis, is reduced by a factor 10 for the A chain issued from modified ricin, whereas it is not altered (or by an unsignificant factor) for the A-1a chain.

2) The difference as regards the pharmacokinetic properties is even more spectacular. The plasma concentration measured 24 h after the injection is 125 times greater for the A-1a chain than for the A chain issued from the modified ricin, of which the capacity to remain in the blood stream is only improved by a factor equal to 2.6 with respect to the native A chain.

The pharmacokinetic results and the results of biological activity of the immunotoxins built with the A chain issued from modified ricin are compiled in Table II which also gives, for comparative purposes, the results obtained with the immunotoxins built with the native A chain and with the A-1a chain prepared according to the invention.

TABLE II

| | Immunotoxin with native A chain | Immunotoxin with A chain issued from modified ricin | Immunotoxin with A-1a chain |
|---|---|---|---|
| Concentration necessary for inhibiting by 50% the synthesis of the proteins from the target cells ($IC_{50}$) | 2,$10^{-10}$M | >$10^{-9}$M | 2,$10^{-10}$M |
| Relative plasma concentration (%) 24 h after the injection | 0.08 | 0.6 | 9 |

These results indicate that:

1) The capacity of A chain immunotoxins issued from modified ricin to remain in the bloodstream in vivo is considerably less than that recorded with the A-1a chain immunotoxins. 24 hours after the injection, the difference corresponds to a factor equal to 15.

2) The cytoxic activity towards the target cells, of the A chain immunotoxins issued from modified ricin, is at least 20 times less than that of the native A chain or A-1a chain immunotoxins which exhibit identical cytotoxic activities. These results show the very great superiority of the immunotoxins prepared according to the invention over those prepared from the intermediates described in the literature.

This comparative test carried out between the works described in the literature and those described in the present application, thus confirms the completely unexpected nature of the results obtained by the Applicant and emphasizes the high degree of improvement brought by the new molecules of A-1a chain and by the new molecules of immunotoxins of A-1a chain.

The following examples are given non-restrictively to illustrate the invention.

EXAMPLE 1

This example demonstrates the slow elimination of the A chain of ricin modified with sodium periodate and by simultaneous reduction reaction with sodium cyanoborohydride after intravenous injection into the animal.

A) Modification of the A chain of ricin by simultaneous action of sodium periodate and sodium cyanoborohydride 1) Blocking of the natural SH with DTNB The A chain of ricin was prepared and purified in the manner indicated in U.S. Pat. No. 4,340,535. 20 equivalents of a solution of 2,2'-dinitro-5,5'-dithio-dibenzoic acid (DTNB), under the form of a solution of DTNB in a 125 mM phosphate buffer (this solution is brought to pH 7 with sodium hydroxide), are added to 20 ml of a solution of A chain of ricin containing 0.81 thiol group per mole of A chain at the concentration of 6 mg/ml, in a 125 mM phosphate buffer, pH 7. Incubation is left to proceed for 30 minutes at 20° C. The solution is then dialyzed against PBS buffer (a buffer 20 mM in respect of phosphate and 150 mM in respect of NaCl, pH 7 ). After centrifuging at 10,000×g for 30 minutes, 107 mg of A chain blocked on the thiol group, are obtained as a solution containing 5.5 mg/ml.

2) Periodate oxidation and reduction by sodium cyanoborohydride of A chain blocked on the thiol group.

The whole of this procedure is carried out at 4 ° C. ml of acetate buffer 0.2 M, pH 6.5 are added to 107 g of A chain blocked on the thiol group contained in 19.5 ml, and this solution is brought to a pH of 6.5 with an acetate buffer 0.2 M of pH 3.5. A solution of sodium cyanoborohydride at 160 mM is prepared in the acetate buffer of pH 6.5. A solution of sodium periodate at 80 mM is prepared in the acetate buffer of pH 6.5, said solution being kept away from the light. Then, 19 ml of the sodium periodate solution are mixed in the dark with 19 ml of sodium cyanoborohydride solution. After 10 minutes, still in the dark, 38 ml of the solution of A chain blocked on the thiol group are added to the mixture of sodium periodate and sodium cyanoborohydride, and incubation is allowed to proceed for 17 hours at 4° C. in the dark. The reaction is stopped by addition of 2.7 ml of a solution of glycerol at 20% (v/v) in the acetate buffer 0.2 M of pH 6.5. Incubation is allowed to continue for 20 hours at 4° C. and the solution is extensively dialysed at 4° C., for 48 hours against an ammonium bicarbonate buffer 50 mM, pH 7.8.

After centrifugation at 10,000×g for 30 minutes, 74 ml of solution at 0.82 mg/ml of A-1a chain blocked on the thiol function and modified on its osidic residues by oxidation and reduction is obtained.

3) Unblocking of the thiol groups.

74 ml of 0.82 mg/ml solution ©f A-1a chain blocked and modified on its osidic units are returned to 16.8 ml by concentration, then 0.406 ml of 2-mercapto-ethanol at 50% are added. Incubation is allowed to proceed for 1 h at 20° C. Then the solution is dialyzed against PBS buffer at 4° C. And 45 mg of modified A-1a chain are obtained of concentration 2.87 mg/ml.

Using the DTNB technique (Methods in Enzymology, 1972, 25, 457 (Academic Press)), it is determined that the modified A chain obtained has 0.79 free thiol group per mol. The molecular weight of the modified A chain is 30,000±3,000, determined by polyacrylamide gradient electrophoresis in the presence of sodium dodecyl-sulfate.

The previously obtained preparation of A-1a chain was studied for its enzymatic activities in the inhibition of protein synthesis and for its pharmacokinetic properties.

B—Enzymatic activity of the prolonged-action A chain, measured on an acellular model The fundamental biological property of the A chain of ricin is to inhibit protein synthesis in cells by degradation of the ribosomal sub-unit 60S.

The in vitro protocol involves the use of appropriately complemented, subcellular fractions of rat liver capable of incorporating $^{14}C$-phenylalanine in the presence of an artificial messenger RNA: polyuridylic acid.

The procedure employed for preparing the subcellular fractions and measuring the incorporation of $^{14}C$-phenylalanine is an adaptation of the method described in Biochemica Biophysica Acta 1973, 312, 608–615, using both a microsomal fraction and a cytosol fraction of the rat hepatocytes. The sample containing the A chain is introduced in the form of a solution appropriately diluted in a 50 mM Tris HCl buffer of pH 7.6 containing 0.2% of 2-mercaptoethanol and 15 micrograms/ml of bovine serum albumin.

The count data are used to calculate, relative to a control medium without inhibitor, the percentage inhibition of the incorporation of $^{14}C$-phenylalanine into the proteins for each reaction medium containing A chain of ricin.

With the curves obtained, it is possible to calculate the $IC_{50}$ or concentration of A chain (native or modified) which inhibits by 50% the incorporation of the radiolabeled precursor in the proteins. An $IC_{50}$ is thus observed which is equal to $1.2.10^{-10}$ mole/l for the A-1a chain according to the invention. The $IC_{50}$ of the control A chain in the experiment is $10^{-10}$ mole/1: considering the precision of the measurements, the modification does not entail any significant loss of activity of the A chain.

C—Pharmacokinetic properties of the prolonged-action A chain modified on its polysaccharide units The A chain (native or modified) is administered to rabbits by means of a single injection into a vein in the ear. The quantity of A chain injected corresponds to 0.415 mg/kg. Blood samples are taken at intervals on heparin. The plasmas are analyzed with the aid of a radioimmunometric test designated below by the abbreviation RIM-1.

This technique has the advantage of determining the A chain without modifying it. This determination is carried out in microtitration plates (for example: "NUNC-TSP screening system" from Poly Labo Block France), the lid of which carries hyperabsorbent spikes which dip into the wells in the base. These spikes constitute the solid phases. Sheep antibodies directed against the A chain of ricin (designated below by the abbreviation Acl), purified by affinity chromatography, are absorbed on the solid phases. For this purpose, 200 microliters of a solution of Acl containing 10 micrograms/ml in PBS phosphate buffer are divided up into the wells.

The spikes are brought into contact firstly with the solution of Acl for 24 h at 4° C. and then with fetal calf serum for 3 h at 20° C. in order to saturate all the fixation sites. The saturated immunoabsorbent is then brought into contact for 3 h at 20° C. with the plasma samples to be determined at different dilutions, or with solutions of A chain of known concentrations in order to establish the calibration curve. After washing with a PBS buffer, the immunoabsorbent is brought into contact for 2 h at 20° C. with the sheep antibodies directed against the A chain of ricin, which have been purified by affinity chromatography and radiolabeled (designated below by the abbreviation Ac2). The radiolabeling of the Ac2 is effected with iodine 125 in the presence of chloramine T by the method of Greenwood and Hunter (Biochem. J., 1963, 89, 114); the specific activity of the radiolabeled Ac2 antibodies is 5 to 10 microcuries/microgram. $10^6$ cpm of radiolabeled Ac2 antibodies are introduced as 200 microliters into a PBS buffer containing 0.1% of bovine serum albumin. After washing in PBS buffer, the spikes are detached and the quantity of bound Ac2 is measured by counting the radioactivity. The concentration of A chain in the samples to be determined is measured by reference to the calibration curve established by introducing the A chain at different known concentrations. When prolonged-action A chain is injected into the animal, this same prolonged-action A chain is used to establish the corresponding calibration curve.

The values of the concentration of A chain(native or modified)in the blood plasma measured by this technique are reproducible and reliable. The detection threshold is 1 nanogram/ml. A study of the reproducibility within and between experiments gives coefficients of variation of less than 10% for concentration values within the range from 1 to 200 nanograms/ml.

The results of these experiments are represented in the form of curves in which the time, expressed in hours, is plotted on the abscissa and the plasma concentration of the product measured, recorded in per cent of the theoretical plasma concentration at time zero, is plotted on a logarithmic scale on the ordinate. This value, called the "relative plasma concentration" (RPC), is calculated using the following expression:

$$RPC = \frac{\text{Concentration measured at time } t}{\text{quantity injected/plasma volume}} \times 100$$

The plasma volume is considered to be equal to 36 ml/kg of the animal's body weight.

FIG. 1 shows the plasma elimination curve, as a function of time, for the native A chain of ricin and for the modified A-1a chain injected intravenously. This curve (curve 1) has two phases: in the first phase, the product disappears very rapidly from the bloodstream since only 0.1% of the dose administered remains in the plasma three hours after injection. In the second phase, the decrease is slower.

When the A chain has been modified on its osidic units (chain A-1a, curve 2), the elimination profile is profoundly modified: the first elimination phase—which is responsible for the disappearance of the majority of the product—is practically suppressed, which leads to a considerable increase in the plasma levels of A chain. Twenty four hours after injection, the concentration of the oxidized A chain is 330 times greater than in the case of the unmodified A chain (curve 2).

These results therefore show that the oxidation reaction with the sodium periodate and the reduction of the aldehyde groups which have appeared with formation of primary alcohol, by the action of the sodium cyanoborohydride, have modified the sugars implicated in the recognition process responsible for the elimination of the A chain to the point of preventing said recognition without the biological activity characteristic of the A chain being altered.

EXAMPLE 2

This example demonstrates the importance of the duration of the oxidative treatment on the pharmacokinetic properties of the oxidized and reduced A chain.

Five preparations of A-1a chain are made using the procedure indicated in Example 1, except for the duration of the treatment by the sodium periodate plus sodium cyanoborohydride treatment. The treatment times are as follows: zero (reaction stopped immediately with glycerol), 30 minutes, 1 hour, 2 hours, 4 hours and 16 hours.

These various preparations are injected into rabbits and the relative plasma concentration of the A-1a chain is measured after 24 hours by the same procedure as in Example 1.

Figure 2:
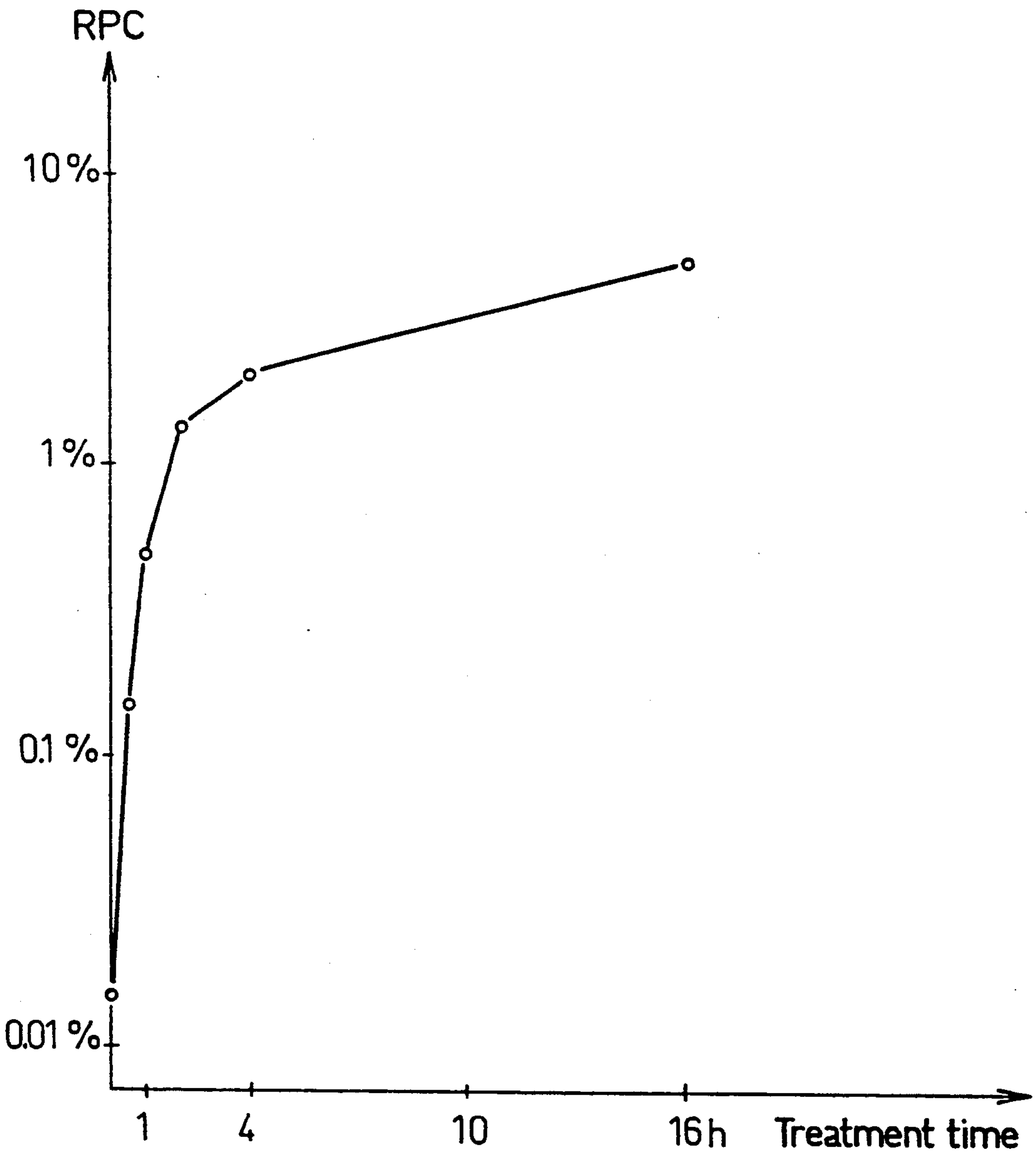
FIG. 2 shows plasma elimination after 24 hours as a function of duration of treatment of the A-chain by oxidation reduction.

The results are shown in FIG. 2, on which the RPC after 24 hours is given in ordinate and the duration of the periodate-cyanoborohydride treatment is given in abscissae.

These results indicate that:

1) the increase in the plasma level of the A chain is indeed due to oxidation and reduction reaction because, when the reaction is stopped immediately, the plasma concentration of A chain is identical to that obtained with the native A chain,
2) it is necessary for the duration of this reaction to be relatively long in order to obtain optimum effects.

EXAMPLE 3

The immunotoxin (abbreviated IT) obtained by reaction between an antibody directed against mice T cells (antibody directed against antigen Thy 1.2) substituted by activated disulfide groups and A-1a chain of ricin:

a) Antibody directed against mice T cells or AT15E antibody

This antibody was obtained according to the method described in Journal of Immunology, 1979, 122, 2491-2498.

b) A-1a chain of ricin

The A-1a chain of ricin which was used was prepared as indicated in Example 1.

c) Activated Antibody directed against mice T cells 4.25 mg of N-succinimidyl-3-(2-pyridyl-dithio)propionate in ethanol at 95% under a volume of 0.5 ml, are added to 10 ml of a 5.83 mg/ml solution of antibody in a borate buffer 0.1 M pH8.8. The mixture is stirred for 30 minutes at 20° C. After dialysis against a 125 mM phosphate buffer of pH 7, the protein solution is centrifuged at 10,000 xg for 30 minutes at 4° C., and 57.3 mg of activated antibody are thus obtained at a concentration of 4.66 mg/ml. By spectrophotometric dosage at 343 nm of 2-pyridinethione liberated by exchange with 2-mercaptoethanol, it is found that an antibody is obtained which carries 3.75 activated mixed disulfide groups per mole of antibody.

d) Preparation of the immunotoxin having the prolongedaction A-1a chain of ricin 8.9 ml of A-1a chain at 2.87 mg/ml obtained as indicated in Example 1 are added to 6.5 ml of the activated antibody solution obtained hereinabove (concentration 4.66 mg/ml, i.e. 30.3 mg of activated antibodies), and incubation is left to proceed for 20 hours at 25° C. The solution is centrifugated, then purified by filtration on a gel (AcA 44 gel) with measurement of the optical density of the effluent at 280 nm. Regrouping of the fractions containing both the antibody and the modified A chain leads to 32 ml of immunotoxin solution at 0.4 mg/ml, i.e. 12.8 mg. This solution contains 0.107 mg of modified A-1a chain coupled to the antibody per ml. The average coupling rate of this preparation is therefore 1.8 mole of A-1a chain per mole of antibody.

The immunotoxin with A-1a chain of ricin obtained as indicated above was studied for its pharmacokinetic properties and its specific cytotoxic properties towards the target cells.

EXAMPLE 4

This example shows how the slow plasma elimination property is acquired by the prolonged-action immunotoxins with A chain of ricin, abbreviated to IT (A-1a).

A) Procedure

The conjugate prepared according to the method described in Example 3 is administered to the rabbit by a single injection in a vein of the ear. The injected quantity corresponds to 0.415 mg/kg expressed in A chain. Blood samples are taken at intervals on heparin. The plasmas are analyzed with the aid of radioimmunometric tests with two sites hereinafter designated by the abbreviation RIM-3.

This assay is carried out by the same technique as that used for the test RIM-1 (described in example 1) except that the solution Ac2 is here a solution of goat antibodies directed against mouse IgG, purified by affinity chromatography and radiolabeled as described for the RIM-1 technique (described in Example 1). The concentration of modified immunotoxin in the samples is measured by reference to a calibration curve established by introducing the modified immunotoxin at different known concentrations. The assay RIM-3 has the same reliability and reproducibility characteristics as described for the RIM-1 technique.

By way of comparison, a control study is carried out under the same conditions with the conjugate called IT-AT15E, which is obtained by the reaction of the same antibody AT15E, substituted by activated disulfide groups, with the native A chain of ricin. The preparation of this conjugate is carried out by the same method as described in Example 3. The results of these pharmacokinetic experiments are represented in the same way as for the uncoupled A chain of ricin in Example 1.

B) Results

Figure 3:
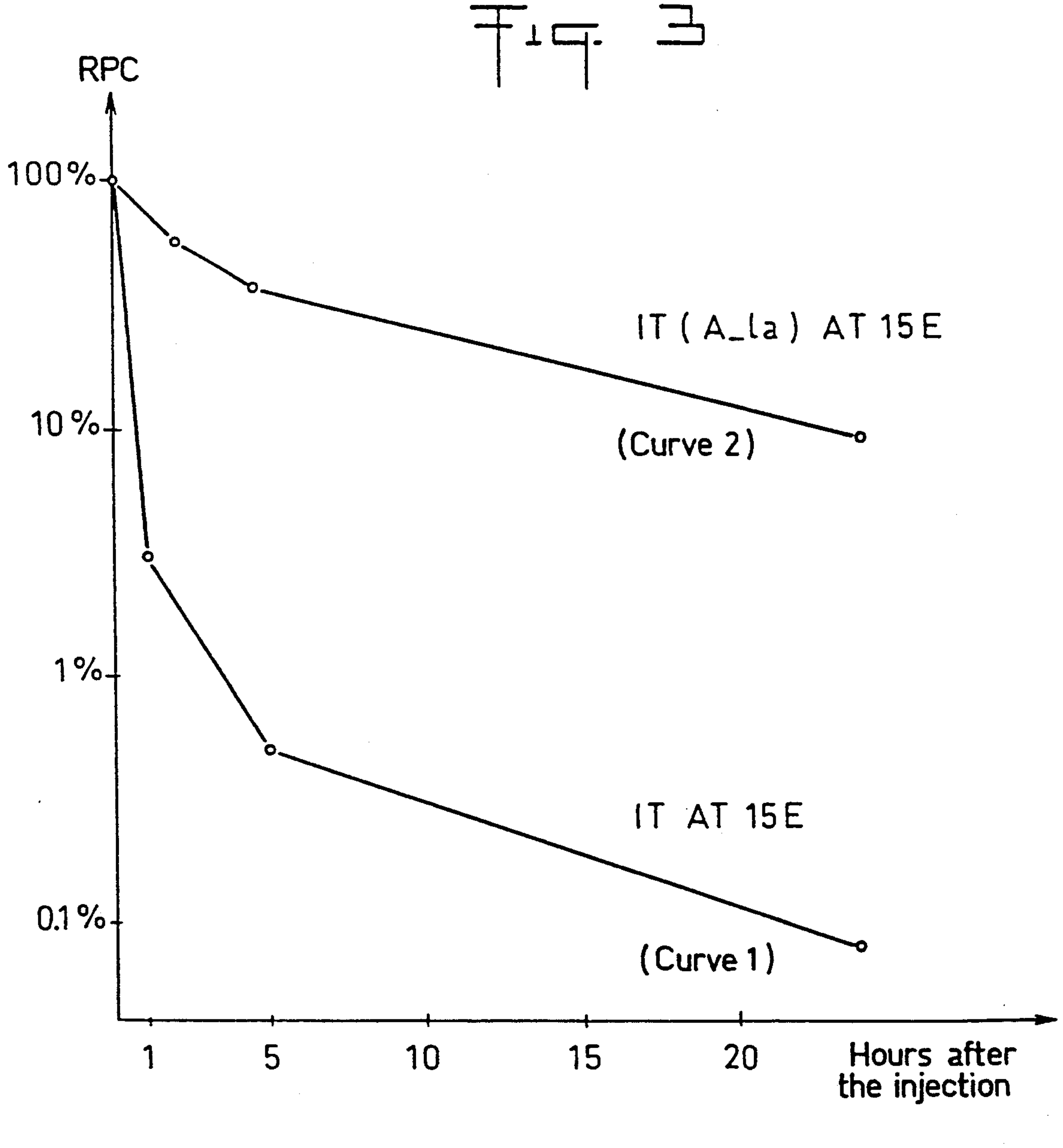
FIG. 3 shows the plasma elimination curves as a function of time for a conventional immunotoxin (curve 1) and a modified immunotoxin conjugate (curve 2) according to the present invention.

FIG. 3 shows the plasma elimination curves, as a function of time, for conventional IT AT15E (curve 1) and IT (A-1a) AT15E (curve 2), injected intravenously. 24 hours after injection, the concentration of active immunotoxin is 110 times greater for IT (A-1a) AT15E than for the conventional ITATi5E This fact demonstrates that the new pharmacokinetic properties of the oxidized A chain are retained after coupling with an antibody.

EXAMPLE 5

This example demonstrates the retention of the specific cytotoxicity properties of IT (A-1a) AT15E towards the positive target cells Thy 1.2.

The fundamental biological property of the A chain of ricin is to inhibit protein synthesis in cells by degradation of the ribosomal sub-unit 60S. The technique uses a cell model in which the effect of the substances studied on the incorporation of $^{14}C$-leucine into cancerous cells in culture is measured.

The cells used belong to the cell line T2 derived from a T leukemia which carries the antigen Thy 1.2. The cells are incubated in the presence of the substance to be studied, and then, when incubation has ended, the degree of incorporation of $^{14}C$-leucine by the cells treated in this way is measured. The experiment is carried out in the presence or in the absence of ammonium chloride at the final concentration, of 10 mM, known to increase the cytotoxic activity of the immunotoxin.

This measurement is made by a technique adapted from the one described in Journal of Biological Chemistry 1974, 249(11), 3557-3562, using the tracer $^{14}C$-leucine to determine the degree of protein synthesis. The radioactivity incorporated is determined here on the whole cells isolated by filtration.

On the basis of these determinations, it is possible to draw the dose/effect curves, plotting, on the abscissa, the molar concentration of A chain in the substances studied, and, on the ordinate, the incorporation of $^{14}C$-leucine expressed as a percentage of the incorporation by control cells in the absence of any substance affecting protein synthesis.

It is thus possible to determine, for each substance studied, the concentration which causes a 50% inhibition of the incorporation of $^{14}C$-leucine, or "50% inhibitory concentration" ($IC_{50}$).

Table II hereinafter represents the values of IC50 obtained in the same experiment with IT (A-1a) AT15E and IT AT15E with or without ammonium chloride on the one hand, and with the native A chain and the uncoupled A-1a chain on the other hand.

It is found that the IT (A-1a) AT15E has a very strong cytotoxic activity, identical to that obtained with the corresponding immunotoxin with native A chain and which is about 1,000 times greater than that of the A-1a chain, measured in the same conditions.

It is also found that the IT (A-1a) AT15E fully retains its capacity to be potentiated by ammonium chloride.

TABLE III

| Products | Inhibiting concentration 50 |
|---|---|
| IT (A-1a) AT15E | $2.10^{-10}$M |
| IT (A-1a) AT15E + 10 mM NH4Cl | $3.10^{-11}$M |
| IT AT15E | $2.10^{-10}$M |
| IT AT15E + 10 mM NH4Cl | $3.10^{-11}$M |
| Native A chain | $3.10^{-7}$M |
| A-1a chain | $2.10^{-7}$M |

EXAMPLE 6

This examples shows, after intravenous injection into the animal, 1) the rapid elimination of native gelonine and
2) the slow elimination of gelonine modified by oxidation reaction with sodium periodate and by simultaneous reduction reaction with sodium cyanoborohydride.

A) Modification of gelonine by the simultaneous action of sodium periodate and sodium cyanoborohydride The gelonine was prepared and purified from Gelonium multiflorum by the method which has been described (J. Biol. Chem. (1980) 255, 6947-6953). The oxidation reaction is carried out under the same conditions as those described for the A chain of ricin in Example 1, except that the step in which the thiols are blocked with DTNB is omitted.

In fact, as the coupling of gelonine with the antibody is not generally performed using natural thiol groups of the gelonine, the thiol groups will be introduced artificially, after the oxidation step, by the technique described in Cancer Res., 1984, 44, 129–133. 1 ml of a 0.2 M acetate buffer, pH 6.5 is added to 1 ml of a solution containing 5 mg/ml of gelonine in PBS buffer, and the pH is brought to 6.5 with 0.2 M acetate buffer pH 3.5. A 160 mM sodium cyanoborohydride solution in acetate buffer pM 8.5 is prepared. A 80 mM sodium periodate solution in an acetate buffer pH 6.5 is prepared and this solution is keeped in the dark. Then. 1 ml of the sodium periodate solution is mixed in the dark with 1 ml of the sodium cyanoborohydride solution. After 10 minutes, 2 ml of the gelonine solution is added in the dark to the mixture of sodium periodate/sodium cyanoborohydride. Incubation is left to proceed for 17 hours at 4° C. in the dark. The reaction is stopped by the addition of 142 microliters of 20 % (v/v) glycerol solution in 0.2 M acetate buffer pH 6.5. Incubation is left to proceed for 20 hours at 4° C., then the reaction medium is dialyzed at 4° C. for 48 hours against an ammonium bicarbonate buffer 50 mM pH 7.8. After centrifugation at 10,000×g for 30 minutes, this gives 2.8 mg of oxidized qelonine at a concentration of 0.7 mg/ml.

Like the A chain of ricin, the fundamental property of gelonine is to inhibit protein synthesis in eucaryotic cells by degradation of the ribosomal sub-unit 60S (Biochem. J., 19S2, 207, 505–509). In the case of gelonine too, the modification does not cause any significant loss of activity.

B) Pharmacokinetic properties of prolonged-action gelonine

Native gelonine or gelonine modified by the procedures explained above is administered to rabbits by a single injection into a vein in the ear. The quantity of gelonine injected is between 0.3 and 0.4 mg/kg. Blood samples are taken at intervals on heparin. The plasmas are analyzed with the aid of a radioimmunometric test designated below by the abbreviation RIM-2.

This test is performed by the same technique as used for the test RIM-1, except that the solution Ac1 here is a solution of anti-gelonine rabbit antibodies purified by affinity chromatography, the Ac2 antibodies being the same antibodies radiolabeled. The radiolabeling procedure is identical to that described for the technique RIM-1 The concentration of native gelonine or modified gelonine in the samples to be determined is measured by reference to a calibration curve established by introducing native or modified gelonine at different known concentrations. The test RIM-2 has the same reliability and reproducibility characteristics as described for the technique RIM-1.

The plasma elimination curves, as a function of time, for native gelonine and modified gelonine, injected intravenously, show that the native gelonine, like the native A chain of ricin, disappears very rapidly from the bloodstream since 89.99 % of the gelonine present in the bloodstream disappears in 24 hours. When the gelonine has been modified on its polysaccharide units, the elimination profile is profoundly modified: 24 hours after injection, the concentration of the modified gelonine is 250 times greater than that of the native gelonine.

Thus, as for the A chain of ricin, these results prove that the sodium periodate oxidation and the reduction of aldehyde groups appeared with the formation of primary alcohol by the action of sodium cyanoborohydride, modified the sugars involved in the recognition process responsible for the elimination of the gelonine, to the point of preventing this recognition.

These modified immunotoxins can be used for the treatment of cancerous or non-cancerous diseases where the target cells would be recognized by the antibody used for preparing the immunotoxin. The optimum administration conditions, and the treatment time will have to be determined in each case according to the subject and to the nature of the disease to be treated. The new drugs according to the invention are presented in a form suitable for the administration by injection and preferably intravenous injection.

What is claimed is:

1. A modified glycoprotein which inactivates ribosomes and having the ribosome-inhibiting activity of the corresponding native glycoprotein which inactivates ribosomes and an in-vivo prolonged action with respect to the corresponding native glycoprotein which inactivates ribosomes, wherein said modified glycoprotein which inactivates ribosomes is obtained by treatment of a glycoprotein which inactivates ribosomes having a molecular weight from about 20,000 to 30,000 with an oxidizing agent to oxidize the osidic groups of said glycoprotein to aldehyde groups which are reduced when said aldehyde groups are formed into stable primary alcohol groups.

2. An immunotoxin having a prolonged action in-vivo, resulting from the coupling of an antibody or antibody fragment with a modified glycoprotein which inactivates ribosomes according to claim 1.

3. An immunotoxin of claim 2, having the following statistical formula:

P'—W—GPIR—'1a' in which P' represents the radical of a protein P, which is an antibody or an antibody fragment, GPIR-1a'represents the radical of a protein GPIR-1a, which is a glycoprotein which inactivates ribosomes, the carbohydrate units of which are modified by oxidation, and W represents a divalent covalent structure containing a thioether group or a disulfide group in which either the sulfur atoms are those of the cysteins of P and GPIR-1a or they are bonded to the groups belonging to P and/or GPIR-1a by spacing structures carrying a functional group bonded to the said groups belonging to P and/or GPIR-1a.

4. The immunotoxin of claim 3 having the following statistical formula:

P'—W—GPIR—1a' in which P' represents the radical of a protein which is a glycoprotein which inactivates ribosomes, GPIR-1a, obtained by treatment of a glycoprotein which inactivates ribosomes, with an aqueous solution of an alkali metal periodate, for a period of 0.2 to 24 hours, at room temperature and in the absence of light, and W represents a divalent covalent structure containing a thioether group or a disulfide group in which the sulfur atoms are either those of the cysteines of P and GPIR-1a or they are bonded to the groups belonging to P and/or GPIR-1a by spacing structures carrying a functional group bonded to the said groups belonging to P and/or GPIR-1a.

5. The immunotoxin of claim 3 in which W is W' which represents a divalent structure chosen from:

(a) a group of the formula

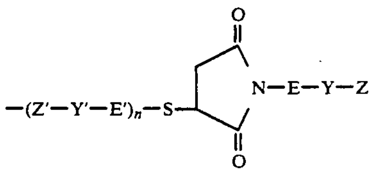

(b) a group of the formula

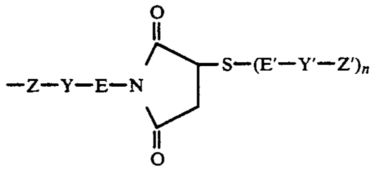

(c) a group of the formula:

—Z—Y—E—S—S—(E'—Y'—Z')$_n$— or (d) a group of the formula:

—(Z'—Y'—E')$_n$—S—S—E—Y—Z—, in which:

Z and Z', are the same or different and represent the groups belonging to the proteins GPIR-1a and P, chosen with the oxygen atom originating from the hydroxyl of one of the tyrosine residues, the carbonyl group originating from one of the terminal carboxyls or one of the free carboxyls of the aspartic and/or glutamic acids of GPIR-1a and P, —NH— group originating from one of the terminal amines of GPIR-1a and P or from one of the amines in the epsilon position of one of the lysine residues, and, only for Z in the covalent structures (b) and (c), the group originating from the dialdehyde structure obtained after oxidation of one of the carbohydrate structures of P with periodic acid;

Y and Y' represent functional groups capable of bonding covalently with any one of the groups Z and Z' of the proteins GPIR-1a and P;

E and E' represent inert spacing structures; and n represents zero or 1.

6. The immunotoxin of claim 5 having the following statistical formula:

P'(W'-A-1a')$_m$ in which m varies from 0.3 to 12, P' represents the radical of a protein P, which is an antibody or an antibody fragment, GPIR-1a' is A-1a' which represents the radical of a glycoprotein which inactivates ribosomes, obtained by treatment of the A chain of ricin, in which at least one of the thio groups of its cysteines 171 and 257 is protected, with an aqueous solution of an alkali metal periodate, for a period of 0.2 to 24 hours, at a temperature of 0° to 15° C. and in the absence of light, and by deprotection of the thio group or thiol groups.

7. An immunotoxin as claimed in claim 6 of the statistical formula:

P'(W'-A-1a')$_m$ in which W' and A-1a' are as defined in claim 6, P' is an antibody fragment Fab or Fab' and m varies from 0.3 to 2.

8. An immunotoxin as claimed in claim 6, of the statistical formula:

P'(W'-A-1a')$_m$ in which W' and A-1a' are as defined in claim 6, P' is an antibody fragment F(ab')$_2$ and m varies from 0.5 to 4.

9. An immunotoxin as toxin as claimed in claim 6, of the statistical formula:

P'(W'-A-1a')$_m$ in which W' and A-1a' are as defined in claim 6, P' is an antibody of the IgG type and m varies with 0. 5 to 6.

10. An immunotoxin as claimed in claim 6, of the statistical formula:

P'(W'-A-1a')$_m$ in which W' and A-1a' are as defined in claim 6, P' is an antibody of the IgM type and m varies from 1 to 12.

* * * * *